US007507416B2

(12) United States Patent
Audonnet et al.

(10) Patent No.: US 7,507,416 B2
(45) Date of Patent: **\*Mar. 24, 2009**

(54) LIVE RECOMBINED VACCINES INJECTED WITH ADJUVANT

(75) Inventors: Jean-Christophe Francis Audonnet, Lyons (FR); Jules Maarten Minke, Corbas (FR)

(73) Assignee: Merial Limited, Duluth, GA (US)

( * ) Notice: Subject to any disclaimer, the term of this patent is extended or adjusted under 35 U.S.C. 154(b) by 559 days.

This patent is subject to a terminal disclaimer.

(21) Appl. No.: 10/735,429

(22) Filed: Dec. 12, 2003

(65) Prior Publication Data

US 2006/0057163 A1 Mar. 16, 2006

Related U.S. Application Data

(63) Continuation-in-part of application No. 09/622,951, filed as application No. PCT/FR99/00453 on Mar. 1, 1999, now Pat. No. 6,713,068.

(30) Foreign Application Priority Data

Mar. 3, 1998 (FR) .................................. 98 02800

(51) Int. Cl.
*A61K 39/145* (2006.01)
*A61K 39/275* (2006.01)
*A61K 39/295* (2006.01)
*A61K 39/39* (2006.01)

(52) U.S. Cl. ............... 424/199.1; 424/209.1; 424/210.1; 424/280.1

(58) Field of Classification Search ............... 424/204.1, 424/230.1, 232.1, 235.1, 199.1
See application file for complete search history.

(56) References Cited

U.S. PATENT DOCUMENTS

| 3,651,213 A | 3/1972 | Wallis et al. |
| 3,790,665 A | 2/1974 | Glass et al. |
| 3,869,546 A | 3/1975 | Lund |
| 3,919,411 A | 11/1975 | Glass et al. |
| 3,920,811 A | 11/1975 | Lund |
| 4,309,413 A | 1/1982 | Field et al. |
| 4,920,213 A | 4/1990 | Dale et al. |
| 5,731,188 A * | 3/1998 | Cochran et al. .......... 435/235.1 |
| 5,820,869 A | 10/1998 | Wasmoen et al. |
| 5,849,303 A | 12/1998 | Wasmoen et al. |
| 5,958,423 A | 9/1999 | Chu |
| 6,004,777 A | 12/1999 | Tartaglia et al. |
| 6,300,118 B1 | 10/2001 | Chavez |

FOREIGN PATENT DOCUMENTS

| EP | 0 283 085 | 9/1988 |
| EP | 0 532 833 | 3/1993 |
| EP | 0 786 518 | 7/1997 |
| EP | 0 329 264 | 8/1999 |
| WO | WO 94/16681 | 4/1994 |
| WO | WO 94/20070 | 9/1994 |
| WO | WO 97/49825 | 12/1997 |
| WO | WO 98/03198 | 1/1998 |

OTHER PUBLICATIONS

Molitor et al., "Potentiating effect of adjuvants on humoral immunity to porcine parvovirus vaccines in guinea pigs," Vet Microbiol. Apr. 1985;10(3):209-18.*
Olsen et al., "Immunogenicity and efficacy of baculovirus-expressed and DNA-based equine influenza virus hemagglutinin vaccines in mice," Vaccine, vol. 15, No. 10, pp. 1149-1156 (1997).*
Oxburgh et al., "Identification of two antigenically and genetically distinct lineages of H3N8 equine influenza virus in Sweden," Epidemiol. Infect, 120, pp. 61-70 (Feb. 1998).*
Regelson et al., "Synthetic Polyelectrolytes and Tumour Inhibitors," Nature, vol. 186, 778-780 (1960).*
Altman et al., "Immunomodifiers in Vaccines," (1989) Advances in Veterinary Science and Comparative Medicine, 33: 301-343.
Aucouturier et al., "Adjuvants Designed for Veterinary and Human Vaccines," (1993) Progress in Vaccinology 4: 1-28.
Chambers et al., (1988) Virology 167(2): 414-421.
Colombovac PMV/Pox (Fort Dodge Animal Health Benelux) Report of 1994 in Compendium Specialties Pharmaceutiques A Usage Veterinaire.
Declaration Under 37 CFR 1.132 of Hsien-Jue Chu from file history of U.S. Appl. No. 08/993,4000, which matured into US Patent No. 5,958,423 (Sep. 28, 1999) (Chu Declaration).
Edelman, "An Update on Vaccine Adjuvants in Clinical Trial," (1992) AIDS Research and Human Retroviruses 8(8): 1409-1411.
Ganne et al., (1994) Virology 12(13): 1190-1196.
Haines et al., "The Bovine Parainfluenza Virus Type-3 (BPIV-3) Hermagglutinin/neuraminidase Glycoprotein Expressed in Baculovirus Protects Calves Against Experimental BPIV-3 Challenge," (1997) Vaccine, 15(6/7): 730-738.
Hannant, (1991) Equine Vet. Suppl. 12: 10-18.
McElrath, "Selection of Potent Immunological Adjuvants for Vaccine Construction," (1995) Seminars in Cancer Biology 6:375-385.
Mumford et al., "Antigenicity and Immunogenicity of Equine Influenza Vaccines Containing a Carbomer Adjuvant" (1994) Epidermiol Infect. 112: 421-437.
Pialoux et al., "A Prime-boost Approach to HIV Preventative Vaccine Using a Recombinant Canary Virus expressing Glycoprotein 160 (MN) Followed by a Recombinant Glycoprotein 160 (MN/LAI)" (1995) AIDS Research and Human Retroviruses, 11(3).
Wilson et al., "Tissue Reaction and Immunity in Swine Immunized with *Actinobacillus pleuropneumoniae* Vaccines," (1995) Can J. Vet. Res. 59: 299-305.
East et al., "Adjuvants for New Veterinary Vaccines," (1993) Progress in Vaccinology vol. 4 Veterinary Vaccines, Springer Verlag, NY, pp. 1-28.

* cited by examiner

*Primary Examiner*—Mary E Mosher
(74) *Attorney, Agent, or Firm*—Judy Jarecki-Black; Merial Limited; Thomas Kowalski, Esq

(57) ABSTRACT

The recombinant live vaccine comprises a viral vector incorporating and expressing in vivo a heterologous nucleotide sequence, preferably a gene of a pathogenic agent, and at least one adjuvant compound chosen from the acrylic or methacrylic polymers and the copolymers of maleic anhydride and an alkenyl derivative. It is in particular a polymer of acrylic or methacrylic acid cross-linked with a polyalkenyl ether of a sugar or polyalcohol (carbomer), in particular cross-linked with an allyl sucrose or with allylpentaerythritol. It may also be a copolymer of maleic anhydride and ethylene cross-linked, for example, with divinyl ether.

7 Claims, 5 Drawing Sheets

FIGURE 1

ATGAAGACAACCATTATTTTGATACTACTGACCCATTGGGTCTACAGTCAAAACCCA
ACCAGTGGCAACAACACAGCCACATTATGTCTGGGACACCATGCAGTAGCAAATGG
AACATTGGTAAAAACAATAACTGATGACCAAATTGAGGTGACAAATGCTACTGAAT
TAGTTCAGAGCATTTCAATAGGGAAAATATGCAACAACTCATATAGAGTTCTAGATG
GAAGAAATTGCACATTAATAGATGCAATGCTAGGAGACCCCCACTGTGATGTCTTTC
AGTATGAGAATTGGGACCTCTTCATAGAAAGAAGCAGCGCTTTCAGCAATTGCTACC
CATATGACATCCCTGACTATGCATCGCTCCGGTCCATTGTAGCATCCTCAGGAACAT
TGGAATTCACAGCAGAGGGATTCACATGGACAGGTGTCACTCAAAACGGAAGAAGT
GGAGCCTGCAAAAGGGGATCAGCCGATAGTTTCTTTAGCCGACTGAATTGGCTAAC
AAAATCTGGAAACTCTTACCCCACATTGAATGTGACAATGCCTAACAATAAAAATTT
CGACAAACTATACATCTGGGGGATTCATCACCCGAGCTCAAACCAACAGCAGACAG
AATTGTACATCCAAGAATCAGGACGAGTAACAGTCTCAACAAAAAGAAGTCAACAA
ACGATAATCCCTAATATCGGATCTAGACCATGGGTCAGGGGTCAATCAGGCAGGAT
AAGCATATACTGGACCATTGTAAAACCTGGAGATATCCTAATGATAAACAGTAATG
GCAACTTAGTTGCACCGCGGGGATATTTTAAATTGAAAACAGGGAAAAGCTCTGTA
ATGAGATCAGATGCACCCATAGACATTTGTGTGTCTGAATGTATTACACCAAATGGA
AGCATCCCCAACGACAAACCATTTCAAAATGTGAACAAAGTTACATATGGAAAATG
CCCCAAGTATATCAGGCAAAACACTTTAAAGCTGGCCACTGGGATGAGGAATGTAC
CAGAAAAGCAAATCAGAGGAATCTTTGGAGCAATAGCGGGATTCATAGAAAACGGC
TGGGAAGGAATGGTTGATGGGTGGTATGGATTCCGATATCAAAACTCGGAAGGAAC
AGGACAAGCTGCAGATCTAAAGAGCACTCAAGCAGCCATCGACCAGATTAATGGAA
AATTAAACAGAGTGATTGAAAGGACCAATGAGAAATTCCATCAAATAGAGAAGGAA
TTCTCAGAAGTAGAAGGGAGAATCCAGGACTTGGAGAAGTATGTAGAAGACACCAA
AATAGACCTATGGTCCTACAATGCAGAATTGCTGGTGGCTCTAGAAAATCAACATAC
AATTGACTTAACAGATGCAGAAATGAATAAATTATTCGAGAAGACTAGACGCCAGT
TAAGAGAAAACGCGGAAGACATGGGAGGTGGATGTTTCAAGATTTACCACAAATGT
GATAATGCATGCATTGGATCAATAAGAAATGGGACATATGACCATTACATATACAG
AGATGAAGCATTAAACAACCGATTTCAAATCAAAGGTGTTGAGTTGAAATCAGGCT
ACAAAGATTGGATACTGTGGATTTCATTCGCCATATCATGCTTCTTAATTTGCGTTGT
TCTATTGGGTCTCATTATGTGGGCTTGCCAAAAAGGCAACATCAGATGCAACATTTG
CATTTGA (SEQ ID NO: 1)

FIGURE 2

```
ATGTATGGTTACTGGCTGGAATGTGTTATTTGTACAGTCATATGTAATGTACCACTCA
ACACGATATATTTATATCGCGGTTGTGTCTAATAACTGTTTTTAAATAAAGAGATAA
GTCGAAATCACAGGCAGTGAAATGCCTTAAAAATGGGTCTCCTGTCTATGTTAGGAA
TCTCTTATTTTAAGTAGTCCCGCGAGACGATTTACATCCCGGGATCACCAACAATCT
GCGATGAGACGATATAGGATGGGACGCGGAATCTACCTTCTCTATATCTGTCTGTTA
TATACATATCTCCAGTTTGGTACTTCGTCGACAACCGCGGTCAGTATTGAAAATAGT
GATAATAGTACTGCGGAGATGTTATCATCTACCAGCATGTCCGCTACCACCCCGATA
TCCCAGCCAACATCTCCATTCACTACTCCAACTAGAAGATCTACAAATATAGCTACA
AGTTCGAGTACCACCCAGGCATCCCAGCCAACATCTACATTAACTACTCTAACTAGA
AGCTCGACAACTATAGCTACAAGTCCGAGTACCACCCAGGCAGCCACATTCATAGG
ATCATCTACCGATTCCAATACCACTTTACTCAAAACAACAAAAAAACCAAAGCGTA
AAAAGAATAAGAATAACGGGGCCAGATTTAAATTAGATTGTGGATATAAGGGGGTT
ATCTACAGACCGTATTTTAGCCCTCTTCAGCTAAACTGTACTCTACCCACAGAACCT
CATATTACCAACCCTATTGACTTCGAGATCTGGTTTAAACCACGCACCAGATTTGGG
GATTTTCTTGGGGATAAAGAAGACTTCGTAGGGAATCATACCCGCACCAGCATATTA
CTATTTAGCAGCCGTAATGGGAGTGTTAATTCCATGGATCTTGGGGACGCGACACTC
GGGATCCTACAATCTAGGATACCAGATTACACATTATATAATATTCCCATACAACAT
ACCGAAGCGATGTCATTGGGAATCAAATCTGTGGAATCTGCCACGTCCGGTGTTTAT
ACATGGCGGGTCTATGGTGGAGATGGACTAAATAAAACAGTGCTAGGACAGGTAAA
TGTATCTGTAGTGGCATATCACCCCCCGAGCGTAAATCTTACACCACGCGCCAGTCT
ATTTAATAAGACCTTTGAGGCGGTATGTGCAGTGGCGAATTACTTCCCGCGATCCAC
GAAACTAACATGGTATCTTGACGGGAAGCCAATAGAAAGGCAATACATTTCAGATA
CGGCAAGTGTATGGATAGATGGACTCATCACCAGAAGTTCTGTGTTGGCTATTCCGA
CAACTGAAACAGATTCCGAGAAACCAGATATACGATGTGATTTGGAATGGCATGAA
AGTCCTGTGTCCTATAAGAGATTCACGAAAAGTGTAGCCCCGGACGTCTATTACCCA
CCTACTGTGTCTGTTACCTTCGCTGATACACGGGCTATATGTGATGTTAAATGTGTAC
CACGGGACGGGATATCCTTGATGTGGAAAATTGGTAACTACCATCTACCAAAAGCA
ATGAGTGCTGATATACTGATCACAGGTCCGTGTATAGAACGTCCAGGTTTGGTCAAC
ATTCAGAGTATGTGTGATATATCAGAAACGGATGGACCCGTGAGTTATACCTGTCAG
ACCATCGGATACCCACCAATTCTACCGGGATTTTACGACACACAAGTCTACGACGCG
TCCCCTGAAATCGTCAGTGAATCAATGTTGGTTAGTGTCGTTGCTGTAATACTAGGA
GCTGTTCTCATCACAGTCTTTATCTTTATTACGGCATTATGTTTATATTATTCTCATCC
CCGGCGATTATAACTCTTATAGTTCGTATAAATTACTTATCATAACCGTGTTTCAGCG
GTTATATTTTTATAACAGTTAATTGTTTACTAATAGTTTACAAAGTCCATCGTTTATA
AAAAACAAGCCCAGTGGTATTATAATCATTCGTATGGATATAAACCGACTCCAATCC
GTGATCTTTGGTAACCCGCGACGTAATTACTCTCACACATTTTAACTAGTCTACGATC
ACCCAGATATAATAAAAAGATTCGCGTGGACATGCAAGGTATGAGGTCTACGTCAC
AGCCGTTGGTCGAGATACCACTGGTAGATATGGAACCACAGCCATCTATACACTCCA
ACGAGCCTAACCCACCGAATAAAATGTTGACGACAGCTATTTCATCGCGTAGGAGT
GGAATTTTTTATTTTCTCTGGGTATGTTTTTTTTCGGAGTTATCCTAACAGCTACTAT
TATAGTATGTACATTCATATTTACAATACCAGTGGATATGCTCCAGATGCCACGCTG
CCCTGAGGAAACGGTGGGTATCAAAAACTGTTGTATCCGACCGATTAGACGCCATGT
TAAATCACACCAAGATCTAGTTGCCACATGTGCCGAATACATGGAACAACCCGCCG
GCCGCATCTGCTGTTGGAGCGCTTATACCATTATTGGACATCTTCAATGGAGATGGG
```

ATATCTACAAACGACTCTCTTTACGATTGTATTCTCTCTGATGAAAAAAAATCGTGT
AATACATCAATGGCCGTATGTCAATCAACATATCTTCCAAATCCCCTAAGTGACTTT
ATTATGCGCGTTAGGCAGATATTTTCTGGAATCCTAAATCATTAATCCATTTACTAAA
TAAATAAACAATACCGTTTAGGTAATTAAACATGATTCTAGTGTTTATTGTCGTATGT
ACGGGCGATGGGTGGATAACAACTCGACAATGATCAATTATATTGATTAACCTTGTA
ATAAATTCGTCGGATTATTGGATATATCGAGATGATATCACATTATTTTCTAATAGC
GTGTGTTTGAAAGTCCACCCTACTAGTGCCATGTGCGCGTTTGATCGAAGAGGCATT
TAATGTTGCCAGAGTTTCAATTCCGTATGTATCGTCGAGTAATCTAGA (SEQ ID NO: 2)

Fig. 2 (CONT'D)

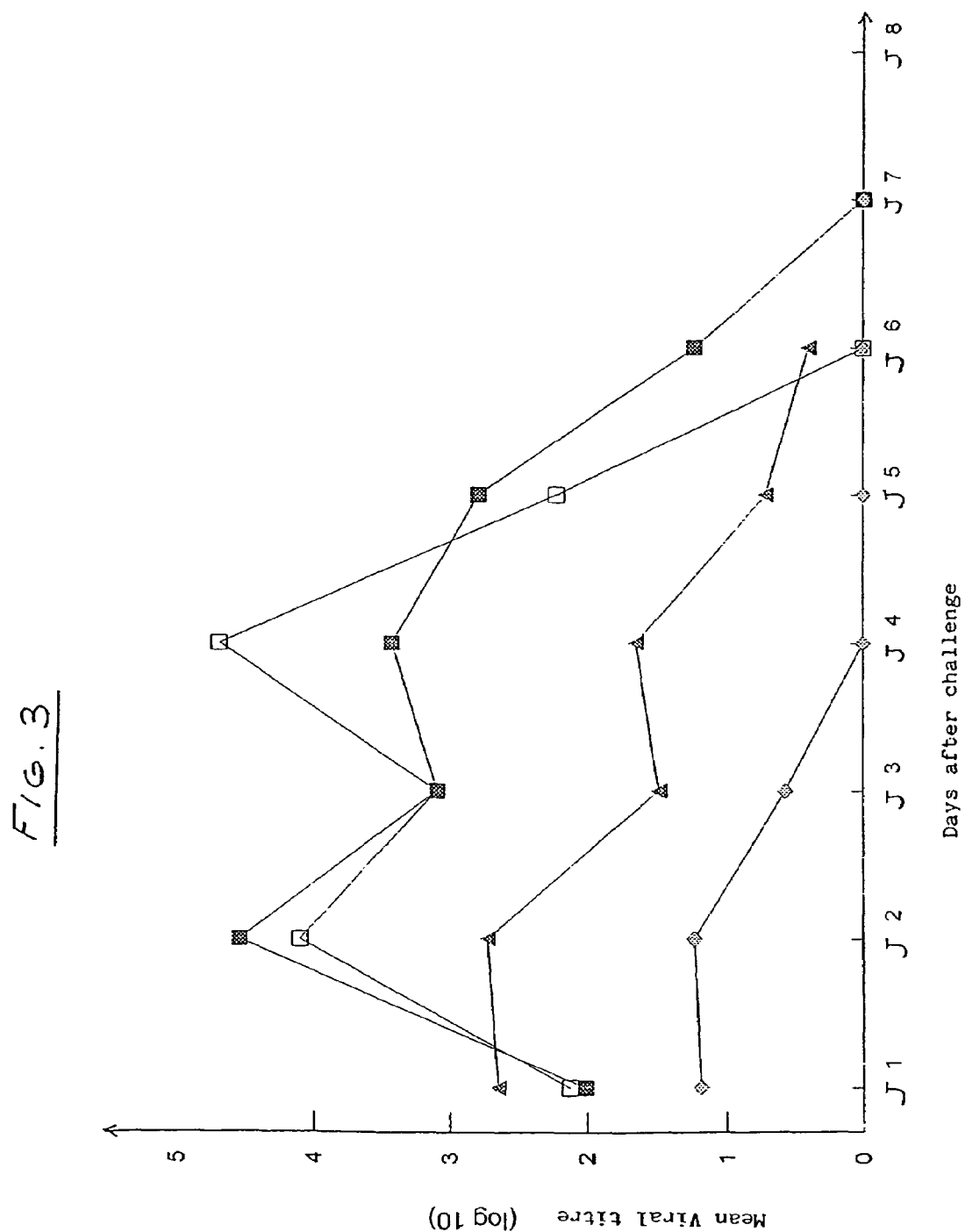

LIVE RECOMBINED VACCINES INJECTED WITH ADJUVANT

REFERENCE TO RELATED APPLICATIONS

This application is a continuation-in-part of U.S. application Ser. No. 09/622,951 filed Oct. 17, 2000 and issued as U.S. Pat. No. 6,713,068 on Mar. 2, 2004, which is the U.S. national phase of international patent application PCT?FR99/00453 filed Mar. 1, 1999 and published as WO 99/44633 on Sep. 10, 1999, which claims priority from French Application 0002800, filed Mar. 3, 1998, each of which are incorporated herein in their entirety by reference.

Additionally, each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference, and may be employed in the practice of the invention. More generally, documents or references are cited in this text, either in a Reference List before the claims, or in the text itself; and, each of these documents or references ("herein cited references"), as well as each document or reference cited in each of the herein cited references (including any manufacturer's specifications, instructions, etc.), is hereby expressly incorporated herein by reference.

In this disclosure, "comprises," "comprising," "containing" and "having" and the like can have the meaning ascribed to them in U.S. Patent law and can mean, "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

BRIEF DESCRIPTION OF THE DRAWINGS

The invention will now be described in greater detail with the aid of the embodiments taken by way of non-limiting examples and referring to the drawings.

FIG. 1 depicts the nucleotide sequence of the EIV HA gene of the EIV Newmarket 2/93 strain.

FIG. 2 depicts the nucleotide sequence of the feline herpesvirus-1 (FHV-1) gc gene.

FIG. 3 depicts a graph showing the variation of viral excretion after experimental injection in horses vaccinated with the aid of different vaccines against EHV. In FIG. 3, ■ represents vCP132 and water (A), ♦ represents vCP132 and carbomer (B), ▲ represents a commercial vaccine (C) and □ represents a control (D).

FIG. 4 is a chart depicting the total clinical scores, including cough, dypsnea, nasal discharge, anorexia and general condition for both the vaccinated and control groups.

The present invention relates to an improvement to recombinant live vaccines integrating and expressing in vivo one or more heterologous genes. It relates in particular to such adjuvant-containing vaccines, to the use of particular adjuvant compounds for using such vaccines as well as to vaccination methods relating thereto. Its subject is also a method of preparing these vaccines.

It is conventional to incorporate into inactivated or subunit vaccines adjuvants intended to increase the immune response towards the antigens which these vaccines contain.

It has also been found to incorporate adjuvants into attenuated live vaccines when the attenuation of microorganisms leads to a reduction in the immune response.

Recently, combined vaccinations against several pathogens using an inactivated vaccine for one valency and an attenuated live vaccine for the other valency have also been proposed. It has thus been proposed to reconstitute the attenuated live vaccine, preserved in freeze-dried form, in the composition of an adjuvant-containing inactivated vaccine. The said composition acts as reconstitution vehicle for the live vaccine, without any adjuvant effect being sought for it.

EP-A-532 833 proposes a vaccine against horse rhinopneumonia, a pathology caused by the equine herpesvirus (EHV). The vaccine is an inactivated and adjuvant-containing vaccine, grouping together the inactivated EHV-4 virus and EHV-1 virus, containing the adjuvant Havlogen®, based on a polyacrylic polymer.

As for most herpesviruses, there is currently no effective vaccine allowing rapid elimination of the virus after infection. The known vaccines attempt to protect against the appearance of clinical signs. In general, the effect on viral excretion remains limited.

According to EP-A-532 833, the vaccine developed is thought to lead to a drop in viral excretion ranging from 79 to 93% (see results section). Eight control animals out of nine excreted virus after a challenge over an average of 1.4 days whereas the normal duration of excretion after challenge is usually greater than or equal to 5 days. This represents a challenge of low intensity which artificially increases the protection of vaccinated horses compared with the controls. The reduction in viral excretion is not therefore significant in this experiment.

Adjuvants of the carbomer type have also been used in inactivated virus-containing equine influenza vaccines (IEV).

- Mumford et al (Epidemiol. Infect. (1994), 112, 421-437) recall that two equine IEV vaccine doses are required to induce a transient humoral response and a weak protection against the virus in horses. The authors compare the adjuvant effects of carbomer and of aluminium phosphate on inactivated vaccines in the presence or otherwise of tetanus toxoid. In all cases, a low antibody titre measured by the SRH (single radial haemolysis) technique with respect to the strains H7N7 and H3N8 is obtained after a first vaccination and a second and then third vaccination are necessary to see the appearance of stronger transient responses.
- U.S. Pat. No. 4,500,513 also presents vaccination trials against the equine influenza virus with an inactivated vaccine in the presence of a carbomer. The origin of the animals and their medical status is not indicated precisely and it appears that they are ground animals (column 11, 2nd paragraph). The high antibody titres, measured by a haemagglutination inhibition technique, indicate that the animals had probably already been infected with influenza and that the response induced after vaccination was of the booster type, and not of the primary vaccination type.

Finally, Fort Dodge Solvay markets inactivated equine influenza vaccines (Duvaxyn® IE and IE-T plus) and an inactivated equine rhinopneumonia vaccine (Duvaxyn® $EHV_{1,4}$), in a carbomer adjuvant.

Commercial inactivated vaccines against equine influenza, containing the adjuvant aluminium hydroxide (for example Tetagripiffa®, Mérial, Lyons, France) are also known.

Figure 4:
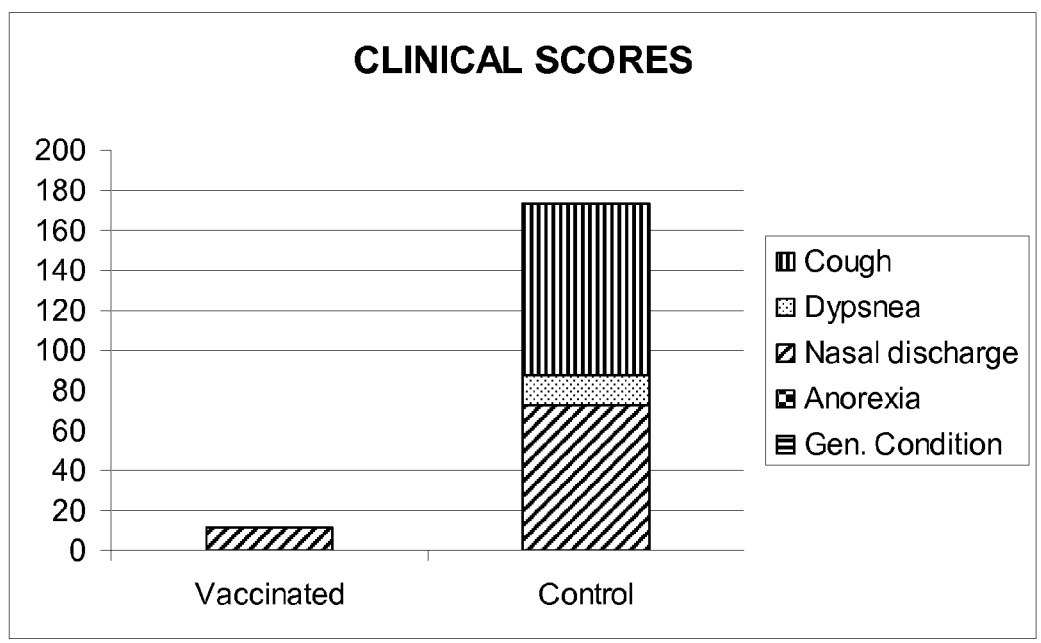

A large number of other adjuvants are used in the context of conventional inactivated or subunit vaccines. There may be mentioned, for example, aluminium hydroxide, aluminium phosphate, Avridine®, DDA, monophosphoryl lipid A, Pluronic L121 and other block polymers, muramyl peptides, saponins, trehalose dimycolate, copolymers of maleic anhydride and ethylene, copolymers of styrene and acrylic or methacrylic acid, polyphosphazene, oily emulsions and the like.

WO-A-94 16681 suggests supplementing a recombinant live vaccine expressing a heterologous gene of an enveloped virus with an adjuvant vaccine composition in the form of a water-in-oil, oil-in-water or water-in-oil-in-water emulsion.

Such a solution may however have a number of disadvantages.

In practice, the final user should have available, on the one hand, a freeze-dried active ingredient and, on the other hand, an already constituted emulsion which should make it possible to reconstitute the freeze-dried active ingredient.

Lack of stability of the emulsion during storage could be detrimental to the efficacy and safety of the reconstituted vaccine.

The activity of attenuated live microorganisms could be called into question following their instability in the oily phase. This may in particular be the case for viruses which may thereby lose their viability.

Vaccines in emulsion can also pose problems of safety at the site of injection.

The present invention is therefore given with the objective of providing new vaccine compositions based on recombinant live vaccine expressing at least one heterologous nucleotide sequence, especially a heterologous gene, containing an adjuvant which is capable of remarkably increasing the immunity conferred relative to the same vaccine with no adjuvant and which is perfectly suitable for this type of vaccine.

The Applicant has found the carbomer class of compounds were capable of acting as adjuvant under the required conditions for this type of vaccine and this in unexpected proportions. Trials carried out on animal herpesviruses (EHV-1, Equine Herpesvirus) have shown that the supply of carbomer could reduce viral excretion during an experimental infection, in unexpected proportions. Other trials carried out on the equine influenza A virus have made it possible to obtain, surprisingly, in horses, early and very high serological titres, better than those obtained with the best commercial vaccines.

The subject of the present invention is therefore a recombinant live vaccine comprising a viral vector incorporating and expressing in vivo a heterologous nucleotide sequence, preferably a gene for a pathogenic agent, and at least one adjuvant compound chosen from the polymers of acrylic or methacrylic acid and the copolymers of maleic anhydride and alkenyl derivative.

The preferred compounds are the polymers of acrylic or methacrylic acid which are cross-linked, especially with polyalkenyl ethers of sugars or polyalcohols. These compounds are known by the term carbomer (Pharmeuropa Vol. 8, No. 2, June 1996). Persons skilled in the art can also refer to U.S. Pat. No. 2,909,462 (incorporated by reference) which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol® (BF Goodrich, Ohio, USA) are particularly appropriate. They are cross-linked with an allyl sucrose or with allyl pentaerythritol. Among them, there may be mentioned Carbopol® 974P, 934P and 971P.

Among the copolymers of maleic anhydride and alkenyl derivative, the copolymers EMA® (Monsanto) which are copolymers of maleic anhydride and ethylene, linear or cross-linked, for example cross-linked with divinyl ether, are preferred. Reference may be made to J. Fields et al., Nature, 186: 778-780, 4 Jun. 1960, incorporated by reference.

From the point of view of their structure, the polymers of acrylic or methacrylic acid and the copolymers EMA® are preferably formed of basic units of the following formula:

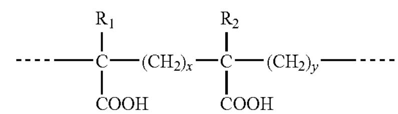

in which:

$R_1$ and $R_2$, which are identical or different, represent H or $CH_3$ x=0 or 1, preferably x=1 y=1 or 2, with x+y=2

For the copolymers EMA®, x=0 and y=2. For the carbomers, x=y=1.

The dissolution of these polymers in water leads to an acid solution which will be neutralized, preferably to physiological pH, in order to give the adjuvant solution into which the vaccine itself will be incorporated. The carboxyl groups of the polymer are then partly in $COO^-$ form.

Preferably, a solution of adjuvant according to the invention, especially of carbomer, is prepared in distilled water, preferably in the presence of sodium chloride, the solution obtained being at acidic pH. This stock solution is diluted by adding it to the required quantity (for obtaining the desired final concentration), or a substantial part thereof, of water charged with NaCl, preferably physiological saline (NaCl 9 g/l), all at once or in several portions with concomitant or subsequent neutralization (pH 7.3 to 7.4), preferably with NaOH. This solution at physiological pH will be used as it is to reconstitute the vaccine, especially stored in freeze-dried form.

The polymer concentration in the final vaccine composition will be 0.01% to 2% w/v, more particularly 0.06 to 1% w/v, preferably 0.1 to 0.6% w/v.

The invention proves particularly useful for vaccination against animal herpesviruses. The invention relates most particularly to the equine herpesvirus (EHV-1 and EHV-4 in particular), feline herpesvirus (FHV), canine herpesvirus (CHV), avian herpesvirus (Marek and ILTV), bovine herpesvirus (BHV) and porcine herpesvirus (PRV=Aujeszky's disease virus or pseudorabies virus).

The subject of the invention is therefore recombinant live vaccines comprising at least one viral vector incorporating and expressing at least one gene of such a herpesvirus and at least one adjuvant in accordance with the invention.

By way of example, persons skilled in the art may refer to WO-A-92 15672 (incorporated by reference), which describes the production of expression vectors based on pox-viruses capable of expressing such genes. There will be found for example a canarypox expressing the gB, gC and gD genes of EHV-1 (vCP132), which is also applicable to EHV-4, a vaccinia virus expressing these same genes (vP 1043), a vaccinia virus expressing the gI(gB), gIII(gC) and gIV(gD) genes of BHV-1, a canarypox expressing gD of FHV-1, or alternatively recombinants expressing the gII (gB), gIII (gC) and gp50 (gD) of PRV. They can also refer to WO-A-95/26 751 (incorporated by reference), which describes recombinant viruses vCP320, vCP322 and vCP294 expressing the gB, gC and gD genes, respectively, of CHV. They can also refer to the recombinants expressing FHV, PRV and BHV genes in FR-A-2 647 808, or WO-A-9012882, incorporated by reference.

The invention also proves particularly advantageous for vaccination against influenza viruses, as demonstrated here for EIV (equine influenza virus) There may also be mentioned avian influenza (AIV), porcine influenza (swine influenza virus).

By way of example, persons skilled in the art can refer to the recombinant canarypox expressing the HA gene of EIV in WO-A-92 15 672.

The subject of the invention is therefore recombinant live vaccines comprising at least one viral vector incorporating and expressing at least one gene of such an influenza virus, and at least one adjuvant in accordance with the invention. In particular, the vaccine comprises a mixture of two or three vectors each incorporating and expressing an HA gene, the genes being obtained from different strains, for example equine influenza strains Prague, Kentucky and Newmarket. Similarly, a single vector may be used to incorporate and express the HAs of 2 or of the 3 strains.

The invention also applies to other animal pathogens, such as in particular FeLV (see also canarypox recombinants in WO-A-92 15672 by way of example, expressing env, gag=vCP93 and vCP97), tetanus (see also WO-A-92 15672 and the recombinants vCP161 and vP1075, canarypox and vaccinia, expressing the tetanus toxin), Carré's disease virus (canine distemper virus or CDV) (see recombinant vCP 258 in WO-A-95 27780, incorporated by reference).

The subject of the invention is therefore recombinant live vaccines comprising at least one viral vector incorporating and expressing at least one gene of such a virus.

The subject of the invention is also multivalent recombinant vaccines, that is to say containing two or more recombinant vectors expressing antigens of two or more diseases, in the form of a mixture in an adjuvant solution in accordance with the invention.

Moreover, the invention applies to the use of any type of viral expression vector, such as poxvirus (vaccinia virus, including NYVAC according to WO-A-92/15672, fowlpox, canarypox, pigeonpox, swinepox and the like), adenovirus, herpesvirus. Canarypox, e.g. ALVAC (WO-A-95/27780 and WO-A-92/15672) is found to be particularly appropriate in the context of the present invention.

In a ready-for-use, especially reconstituted, vaccine, the viral vector is present in the quantities normally used and described in the literature.

The recombinant live vaccines generally exist in a freeze-dried form allowing their storage and are reconstituted immediately before use in a solvent or excipient, which will be here the solution of adjuvant in accordance with the invention.

The subject of the invention is therefore also a vaccination set comprising, packaged separately, freeze-dried vaccine and a solution of the adjuvant compound according to the invention for the reconstitution of the freeze-dried vaccine.

The subject of the invention is also a method of vaccination consisting in administering, by the parenteral, preferably subcutaneous, intramuscular or intradermal, route or by the mucosal route a vaccine in accordance with the invention at the rate of one or more administrations, optionally with a preliminary step of reconstituting the freeze-dried vaccine (the recombinant vector) in a solution of adjuvant compound.

One objective of such a method may be to protect animals from the clinical point of view and to reduce viral excretion, which corresponds in particular to the case of herpesviruses.

Another objective may be to increase the immune response and to make it occur earlier, especially by inducing antibodies starting from the first administration.

The subject of the invention is also the use of the adjuvant compounds in accordance with the invention for the production of recombinant live vaccines, especially conferring an improved and earlier immune response and/or an increased reduction in viral excretion. Reference may be made to what was said above.

The invention will now be described in greater detail with the aid of the embodiments taken by way of nonlimiting examples and referring to the drawing in which:

FIG. 1 represents the nucleotide sequence of the EIV HA gene of the EIV Newmarket 2/93 strain;

FIG. 2 represents the nucleotide sequence of the FHV-1 gC gene;

FIG. 3 represents a graph showing the variation of viral excretion after experimental infection in horses vaccinated with the aid of different vaccines against the equine herpesvirus.

EXAMPLES

Example 1

Generation of the Donor Plasmids for the Sites of Insertion C3, C5 and C6 into the Canarypox Virus "ALVAC"

The donor plasmids for the different sites of insertion into the canarypox virus "ALVAC" (Tartaglia et al. Virology. 1992. 188. 217-232, incorporated by reference) are described in Application WO-A-95/27780, Example 20.

These plasmids were designated in this application in the following manner:
"plasmid VQH6CP3LSA.2" for the "C3" site
"plasmid HC5LSP28" for the "C5" site
"plasmid pC6L" for the "C6" site Example 2

Generation of the Recombinant Virus vCP258 (ALVAC/CDV HA+F)

The Onderstepoort strain of the CDV virus was used to isolate the HA and F genes (sequence of the HA gene described by Curran et al. Virology. 1991. 72. 443-447, and sequence of the F gene described by Barrett et al. Virus Research. 1987. 8. 373-386, both incorporated by reference).

The construction of the donor plasmid pMM103 for the insertion of the expression cassettes H6 vaccinia promoter-CDV F gene and H6 vaccinia promoter-CDV HA gene into the C6 locus of the ALVAC virus is described in Example 19 of Application WO-A-95/27780.

This plasmid was used as donor plasmid for in vitro recombination (Piccini et al. Methods in Enzymology. 1987. 153. 545-563, incorporated by reference), with the ALVAC virus to generate the recombinant virus designated vCP258 as in Example 19 of the abovementioned application.

Example 3

Generation of the Recombinant Virus vCP1502 (ALVAC/EIV HA Prague)

The sequence of the HA gene (EIV Prague strain) is presented in FIG. No. 23 of Application WO-A-92/15672. The viral RNA of the genome of the equine influenza virus strain Prague 56 was extracted from 100 µl of a viral suspension of this virus with the "Total RNA Separator kit" extraction kit from CLONTECH (Palo Alto, Calif.) (Cat#K1042-1). The RNA pellet was taken up in 10 µl of ultrapure water and a complementary DNA synthesis reaction, followed by a PCR reaction (="RT-PCR" reaction) was carried out taking as template 2 µl of purified viral RNA and the following oligonucleotides:

```
                                          (SEQ ID No.1)
TAY51A (70 mer)
5'CGCGGCCATCGCGATATCCGTTAAGTTTGTATCGTAATGAACACTCAA
ATTCTAATATTAGCCACTTCGG3'
``` and

```
                                          (SEQ ID No.2)
TAY53A (36 mer)
5'CGCGCGGCGGTACCTTATATACAAATAGTGCACCGC3'
``` in order to amplify the Prague EIV HA gene. The PCR fragment thus obtained was ligated into the vector PCRII (Invitrogen, San Diego, Calif.) to give the plasmid pJT007.

The plasmid pJT007 was digested with NruI and Asp718 in order to isolate an NruI-718 fragment of about 1800 bp containing the end of the H6 promoter and the Prague 56 HA gene in its entirety. This fragment was ligated with the donor plasmid C5 HC5LSP28, previously digested with NruI and Asp718, to finally give the plasmid pJT008. This plasmid contains the expression cassette H6-Prague 56 HA gene in the C5 locus of the ALVAC virus. The structure of this plasmid was verified by sequencing and complete restriction map.

This plasmid is the donor plasmid for the insertion of the expression cassette H6-Prague 56 HA gene into the C5 locus.

After linearizing with NotI, the plasmid pJT008 was used as donor plasmid for in vitro recombination (Piccini et al. Methods in Enzymology. 1987. 153. 545-563) with the ALVAC virus in order to generate the recombinant virus designated vCP1502.

Example 4

Generation of the Recombinant Virus vCP1529 (ALVAC/EIV HA Kentucky 1/94)

The viral RNA of the genome of the equine influenza virus strain Kentucky 1/94 (Daly et al. J. Gen. Virol. 1996. 77. 661-671, incorporated by reference) was extracted with 100 µl of a viral suspension of this virus with the "Total RNA Separator kit" extraction kit from CLONTECH (Palo Alto, Calif.) (Cat#K1042-1). The RNA pellet was taken up in 10 µl of ultrapure water and RT-PCR reaction was carried out taking as template 2 µl of purified viral RNA and the following oligonucleotides:

```
                                          (SEQ ID No.3)
TAY55A (70 mer)
5'CGCGGCCATCGCGATATCCGTTAAGTTTGTATCGTAATGAAGACAACC
ATTATTTTGATACTACTGACCC3'
``` and

```
                                          (SEQ ID No.4)
TAY57A (42 mer)
5'CGCGCGGCGGTACCTCAAATGCAAATGTTGCATCTGATGTTG3'
``` in order to amplify the HA gene. The PCR fragment thus obtained was ligated into the vector pCRII (Invitrogen, San Diego, Calif.) to give the plasmid pJT001. The sequence of the Kentucky 1/94 strain EIV HA gene cloned into the plasmid pJT001 is not different from the sequence of the Kentucky 1/94 strain EIV HA gene available in the GenBank databank (accession number L39914, incorporated by reference).

The plasmid pJT001 containing the HA gene (Kentucky 1/94) was digested with NruI and Asp718 in order to isolate an NruI-Asp718 fragment of 1800 bp (containing the end of the H6 promoter and the Kentucky 1/94 HA gene in its entirety). This fragment was ligated with the donor plasmid C5 HC5LSP28, previously digested with NruI and Asp718, to finally give the plasmid pJT005. This plasmid contains the expression cassette H6-Kentucky 1/94 HA gene in the C5 locus of the ALVAC virus. The structure of this plasmid was verified by sequencing and complete restriction map.

This plasmid is a donor plasmid for the insertion of the expression cassette H6-Kentucky 1/94 HA gene into the C5 locus.

After linearizing with NotI, the plasmid pJT005 was used as donor plasmid for in vitro recombination (Piccini et al. Methods in Enzymology. 1987. 153. 545-563) with the ALVAC virus in order to generate the recombinant virus designated vCP1529.

Example 5

Generation of the Recombinant Virus vCP1533 (ALVAC/EIV HA Newmarket 2/93)

The viral RNA of the genome of the equine influenza virus strain Newmarket 2/93 (Daly et al. J. Gen. Virol. 1996. 77. 661-671) was extracted from 100 µl of a viral suspension of this virus with the "Total RNA Separator kit" extraction kit from CLONTECH (Cat#K1042-1). The RNA pellet was taken up in 10 µl of ultrapure water and an RT-PCR reaction was carried out taking as template 2 µl of purified viral RNA and the following oligonucleotides:

```
                                          (SEQ ID No.5)
CCL007 (40 mer)
5'TTGTCGACTCAATCATGAAGACAACCATTATTTTGATACT3'
``` and

```
                                          (SEQ ID No.6)
CCL0018 (34 mer)
5'TTGGATCCTTACTCAAATGCAAATGTTGCAYCTG3'
``` in order to amplify the HA gene. The PCR fragment thus obtained was ligated to the vector pCRII (InVitrogen, San Diego, Calif.) to give the plasmid pCCL026. The sequence of the HA gene (EIV Newmarket 2/93 strain) is presented in FIG. No. 1 (SEQ ID No.7).

The plasmid pCCL026 containing the HA gene (Newmarket 2/93 strain) was digested with SpeI and AccI. The following oligonucleotides:

TAY99N (74 mer) (SEQ ID No.8)
5'CTAGTTCGCGATATCCGTTAAGTTTGTATCGTAATGAAGACAACCATT
ATTTTGATACTACTGACCCATTGGGT3' and

TAY100N (72 mer) (SEQ ID No.9)
5'AGACCCAATGGGTCAGTAGTATCAAAATAATGGTTGTCTTCATTACGA
TACAAACTTAACGGATATCGCGAA3' were annealed and ligated with the plasmid pCCL026 digested with SpeI+AccI to give the plasmid pJT003. The double-stranded oligonucleotide TAY99N/TAY100N contains the 3' region of the H6 promoter up to the NruI site and the first 40 coding bases of the HA gene.

The plasmid JT003 was digested with NruI and XhoI in order to isolate an NruI-XhoI fragment of about 1800 bp containing the end of the H6 promoter and the HA gene in its entirety. This fragment was ligated with the donor plasmid C5 HC5LSP28, previously digested with NruI and XhoI, to finally give the plasmid pJT004. This plasmid contains the expression cassette H6-Newmarket 2/93 HA gene in the C5 locus of the ALVAC virus. The structure of this plasmid was verified by sequencing and complete restriction map.

This plasmid is the donor plasmid for the insertion of the expression cassette H6-Newmarket 2/93 HA gene into the C5 locus.

After linearizing with PvuI, the plasmid pJT004 was used as donor plasmid for the in vitro recombination (Puccini et al. Methods in Enzymology. 1987. 153. 545-563) with the ALVAC virus in order to generate the recombinant virus designated vCP1533.

Example 6

Generation of the Recombinant Virus vCP132 (ALVAC/EHV-1 gB+gC+gD)

The construction of the recombinant virus is described in Examples 25 and 26 of Application WO-A-92/15672. This virus was generated by in vitro recombination between the ALVAC virus and the donor plasmid pJCA049. This plasmid contains the following 3 expression cassettes cloned into the site of insertion C3:
I3L vaccinia promoter-EHV-1 gB gene
H6 vaccinia promoter-EHV-1 gC gene
42K entomopox promoter-EHV-1 gD gene The sequences of the EHV-1 gB, gC and gD genes are described in Application WO-A-92/15672 in FIGS. No. 2 (sequence of the EHV-1 gene gp13 =gC), No. 6 (sequence of the EHV-1 gene gp14=gB) and No. 12 (sequence of the EHV-1 genes gD, gp63 and gE).

Example 7

Generation of the Recombinant Virus vCP243 (ALVAC/FHV-1 gB+gC+gD)

The sequence of the FHV-1 gB gene (CO strain) is presented in FIG. No. 34 of Application WO-A-90/12882.

The FHV-1 gC gene (CO strain) (sequence presented in FIG. No. 2) (SEQ ID No. 10) was cloned from the EcoRI F fragment (7.6 kbp). It has a size of 1599 bp and encodes a protein of 533 amino acids.

The FHV-1 gD gene (CO strain) (sequence presented in FIG. No. 28 of Application WO-A-92/15672) was cloned from the EcoRI M fragment (4.4 kbp) (plasmid pFH-VEcoRIM).

Construction of the Expression Cassette I3L-FHV-1 gB Gene Mutated at the Level of the Signals for Early Termination of Transcription (TTTTTNT).

The following oligonucleotides:

MP287 (20 mer) (SEQ ID No.11)
5'GATTAAACCTAAATAATTGT3' and

JCA158 (21 mer) (SEQ ID No.12)
5'TTTTTCTAGACTGCAGCCCGGGACATCATGCAGTGGTTAAAC3' were used for a PCR amplification with the template of a plasmid containing the I3L vaccinia promoter (Riviére et al. J. Virol. 1992. 66. 3424-3434, incorporated by reference) in order to generate a blunt-ended XbaI fragment of 120 bp (containing the I3L vaccinia promoter)=fragment A. The following oligonucleotides:

JCA213 (18 mer) (SEQ ID No.13)
5'GGGTTTCAGAGGCAGTTC3' and

JCA238 (21 mer) (SEQ ID No.14)
5'ATGTCCACTCGTGGCGATCTT3' were used to generate, by PCR from the template of the plasmid pJCA001, a blunt-ended BamHI fragment of 720 bp (containing the 5' part of the FHV-1 gB gene)=fragment B.

Fragment A was digested with XbaI, and then phosphorylated. Fragment B was digested with BamHI, and then phosphorylated. Fragments A and B were then ligated together with the vector pBluescript SK+, previously digested with XbaI and BamHI, to give the plasmid pJCA075.

The following oligonucleotides:
JCA158 (SEQ ID No.15) and JCA211 (SEQ ID No.16) (21 mer):

5'GTGGACACATATAGAAAGTCG3' were used to generate, by PCR from the template of the plasmid pJCA075, a blunt-ended XbaI fragment of 510 bp (containing the I3L promoter fused to the 5' part of the FHV-1 gB gene mutated at the level of the signal TTTTTNT)=fragment C.

The following oligonucleotides:

JCA212 (21 mer) (SEQ ID No.17)
5'CACCTTCAGGATCTACTGTCG3' and JCA213 (SEQ ID No.13) (18 mer)

were used to generate, by PCR from the template of the plasmid pJCA001, a blunt-ended BamHI fragment of 330 bp (containing the central part of the FHV-1 gB gene)=fragment D.

Fragment C was digested with XbaI, and then phosphorylated. Fragment D was digested with BamHI, and then phosphorylated. Fragments C and D were then ligated together with the vector pBluescript SK+, previously digested with XbaI and BamHI to give the plasmid pJCA076.

The following oligonucleotides:

```
                                          (SEQ ID No.18)
    JCA239 (24 mer)
    5'ACGCATGATGACAAGATTATTATC3' and (SEQ ID No.19)
    JCA249 (18 mer)
    5'CTGTGGAATTCGCAATGC3'
``` were used to generate, by PCR from the template of the plasmid pJCA001, a blunt-ended EcoRI fragment of 695 bp (containing the first 3' part of the FHV-1 gB gene)=fragment E. The following oligonucleotides:

```
                                          (SEQ ID No.20)
JCA221 (48 mer)
5'AAAACTGCAGCCCGGGAAGCTTACAAAAATTAGATTTGTTTCAGTATC
3' and (SEQ ID No.21)
JCA247 (36 mer)
5'GGTATGGCAAATTTCTTTCAGGGACTCGGGGATGTG3'
``` were used to generate, by PCR from the template of the plasmid pJCA001, a blunt-ended PstI fragment of 560 bp (containing the second 3' part of the FHV-1 gB gene mutated at the level of the signal TTTTTNT)=fragment F.

Fragment E was digested with EcoRI, and then phosphorylated. Fragment F was digested with PstI, and then phosphorylated. Fragments E and F were then ligated together with the vector pIBI24 (International Biotechnologies Inc., New Haven, Conn.), previously digested with EcoRI and PstI, to give the plasmid pJCA077 (containing the cassette I3L vaccinia promoter FHV-1 B gene).

Construction of the Expression Cassette 42K-FHV-1 gD

The following oligonucleotides:

```
                                          (SEQ ID No.22)
    RG286 (17 mer)
    5'TTTATATTGTAATTATA3' and (SEQ ID No.23)
    M13F (17 mer)
    5'GTAAAACGACGGCCAGT3'
``` were used to generate, by PCR from the template of the plasmid containing the 42K Entomopoxvirus AmEPV promoter (described in Example 21 of U.S. Pat. No 5,505,941), a blunt-ended EcoRI fragment of 130 bp (containing the 42K entomopox promoter)=fragment A. The following oligonucleotides:

```
                                          (SEQ ID No.24)
    JCA234 (21 mer)
    5'ATGATGACACGTCTACATTTT3' and (SEQ ID No.25)
    JCA235 (21 mer)
    5'TGTTACATAACGTACTTCAGC3'
``` were used to generate by PCR from the template of the plasmid pFHVEcoRIM, a blunt-ended BamHI fragment of 185 bp (containing the 5' part of the FHV-1 gD gene)=fragment B. Fragment A was digested with EcoRI, and then phosphorylated. Fragment B was digested with BamHI, and then phosphorylated. Fragments A and B were then ligated together with the vector pBluescript SK+, previously digested with EcoRI and BamHI, to give the plasmid pJCA078.

The plasmid pFHVEcoRIM (see above) was digested with BamHI and XhoI in order to isolate the BamHI-XhoI fragment of 1270 bp (containing the 3' part of the FHV-1 gD gene). This fragment was then ligated with the vector pIBI24, previously digested with BamHI and XhoI, in order to give the plasmid pJCA072. The following oligonucleotides:

```
                                          (SEQ ID No.26)
JCA242 (18 mer)
5'GAGGATTCGAAACGGTCC3' and (SEQ ID No.27)
JCA237 (53 mer)
5'AATTTTCTCGAGAAGCTTGTTAACAAAAATCATTAAGGATGGTAGATT
GCATG3'
``` were used to generate, by PCR from the pFHVEcoRIM template, an XbaI-XhoI fragment of 290 bp. This fragment was digested with XbaI and XhoI=fragment C (containing the end of the FHV-1 gD gene).

The plasmid pJCA072 was digested with XbaI and XhoI in order to isolate the XbaI-XhoI fragment of 3575 bp (vector pIBI24+start of the 3' part of the FHV-1 gD gene)=fragment D. Fragments C and D were then ligated together in order to give the plasmid pJCA073.

The plasmid pJCA073 was digested with BamHI and XhoI in order to isolate the BamHI-XhoI fragment of 960 bp (containing the 3' part of the FHV-1 gD gene)=fragment A. The plasmid pJCA078 was digested with HpaI and BamHI in order to isolate the HpaI-BamHI fragment of 310 bp (containing the 42K promoter fused to the 5' part of the FHV-1 gD gene)=fragment B. Fragments A and B were ligated together with the vector pBluescript SK+, previously digested with EcoRV and XhoI, in order to give the plasmid pJCA080 (containing the cassette 42K promoter-FHV-1 gD gene).

Construction of the Cassette H6-FHV-1 gC

The genomic DNA of the FHV-1 virus (CO strain) was digested with EcoRI and the EcoRI F fragment of about 7500 bp was cloned into pBluescript SK+ to give the plasmid pFHVEcoRIF. The following oligonucleotides:

```
                                        (SEQ ID No.28)
JCA274 (55 mer)
5'CATTATCGCGATATCCGTTAAGTTTGTATCGTAATGAGACGATATAGG
ATGGGAC3' and (SEQ ID No.29)
JCA275 (18 mer)
5'ACTATTTTCAATACTGAC3'
``` were used to generate, by PCR from the pFHVEcoRIF template, a fragment which was digested with NruI and SalI in order to give an NruI-SalI fragment of 107 bp (containing the 3' part of the H6 vaccinia promoter fused to the 5' part of the FHV-1 gC gene)=fragment A.

The following oligonucleotides:

```
                                        (SEQ ID No.30)
JCA276 (18 mer)
5'AAATGTGTACCACGGGAC3' and
```

-continued (SEQ ID No.31)
JCA277 (54 mer)
5'AAGAAGCTTCTGCAGAATTCGTTAACAAAAATCATTATAATCGCC
GGGGATGAG3' were used to generate, by PCR from the pFHVEcoRIF template, a fragment which was digested with EcoRV and HindIII in order to give an EcoRV-HindIII fragment of 370 bp (containing the 3' part of the FHV-1 gC gene and the HpaI-EcoRI-PstI-HindIII sites)=fragment B.

The plasmid pJCA020 (see above) was digested with NruI and HindIII in order to isolate the HindIII-NruI fragment (containing the 5' part of the H6 vaccinia promoter)=fragment C. The plasmid pFHVEcoRIF was digested with BamHI and EcoRV in order to isolate the BamHI-EcoRV fragment of 580 bp (containing the central part of the FHV-1 gC gene)=fragment D. Fragments A and C were ligated together with the vector pBluescript SK+, previously digested with HindIII and SalI in order to give the plasmid pJCA097. Fragments B and D were ligated together with the vector pBluescript SK+, previously digested with BamHI and HindIII, to give the plasmid pJCA099.

The plasmid pJC097 was digested with PstI and SalI in order to isolate the PstI-SalI fragment of 200 bp (containing the cassette H6-5' part of gC)=fragment E. The plasmid pFHVlEcoRIF was digested with BamHI and SalI in order to isolate the SalI-BamHI fragment of 600 bp (2nd central part of FHV-1 gC)=fragment F. Fragments E and F were then ligated together with the vector pBluescript SK+, previously digested with BamHI and PstI, in order to give the plasmid pJCA098. The plasmid pJCA098 was then digested with EcoRI and BamHI in order to isolate the EcoRI-BamHI fragment of 820 bp (containing the cassette H6-5' part of FHV-1gC)=fragment G. The plasmid pJCA099 (see above) was digested with BamHI and HindIII in order to isolate the BamHI-HindIII fragment of 960 bp (containing, the 31' part of the FHV-1 gC gene)=fragment H. Fragments G and H were then ligated together with the vector pBluescript SK+, previously digested with EcoRV and HindIII, in order to give the plasmid pJCA100 (containing the expression cassette H6 vaccinia promoter-FHV-1 gC gene).

The plasmid pJCA100 was digested with NruI and EcoRI in order to isolate the NruI-EcoRI fragment of 1650 bp containing the 3' part of the H6 promoter fused with the FHV-1 gC gene. This fragment was ligated with the plasmid pJCA053 (cassette VQH6-IBV M in the vector pBluescript SK+), previously digested with NruI and EcoRI, in order to give the plasmid pJCA108 (containing the cassette VQH6-gC in pBluescript SK+). The plasmid pJCA079 (see above) was digested with SmaI and BamHI in order to isolate the BamHI-SmaI fragment of 840 bp (containing the cassette I3L-5' part of the FHV-1 gB gene)=fragment A. The plasmid pJCA079 was also digested with BamHI and HindIII in order to isolate the BamHI-HindIII fragment of 2155 bp (containing the 3' part of the FHV-1 gB gene) fragment B. The plasmid pJCA108 (see above) was digested with HindIII and EcoRI in order to isolate the HindIII-EcoRI fragment of 1830 bp (containing the cassette VQH6-FHV-1 gC)=fragment C. The plasmid pJCA080 (see above) was digested with EcoRI and XhoI in order to isolate the EcoRI-XhoI fragment of 1275 bp (containing the cassette 42K-FHV-1 gD gene)=fragment D. Fragments A, B, C and D were then ligated together with the donor plasmid pC6L in order to give the plasmid pJCA109.

This plasmid contains the expression cassettes H6-FHV-1 gene gC, I3L-FHV-1 gB gene and 42K-FHV-1 gD gene in the C6 locus of the ALVAC virus. The structure of this plasmid was verified by sequencing and complete restriction map.

This plasmid is the donor plasmid for the insertion of the expression cassettes H6-FHV-1 gC gene, I3L-FHV-1 gB gene and 42K-FHV-1 gD gene in the C6 locus of the ALVAC virus.

After linearizing with NotI, the plasmid pJCA109 was used as donor plasmid for in vitro recombination (Piccini et al. Methods in Enzymology. 1987. 153. 545-563) with the ALVAC virus in order to generate the recombinant virus designated vCP243.

Example 8

Adjuvant

The carbomer used in the vaccines in accordance with the present invention is Carbopol® 974P manufactured by the company BF Goodrich (MW about 3 million).

A stock solution containing 1.5% w/v of Carbopol® 974P was first prepared in distilled water containing sodium chloride at 1 g/l.

This stock solution is then used for the manufacture of a solution of Carbopol® in physiological saline at 4 mg/ml. The stock solution is poured into the entire physiological saline (or optionally into most of it) all at once or optionally in several portions with, each time, adjustment of the pH with the aid of NaOH (for example 1 N or more concentrated) to a value of about 7.3 to 7.4.

A ready-for-use solution of Carbopol® is thereby obtained which can be used by the final user to reconstitute a freeze-dried recombinant vaccine.

Example 9

Vaccination of Horses with the Aid of the Recombinant Canarypox Vector vCP132 (see Example 6) Expressing the Glycoproteins gB, gC and gD of the Type I Equine Herpesvirus (EHV-1).

1. Protocol for Immunization and Challenge:

20 ponies (Welsh mountain ponies) exhibiting no serological signs indicating a recent exposure to EHV-1 and EHV-4 were randomly distributed into 4 groups (A to D) of 5 ponies.

Groups A and B were vaccinated with the recombinant canarypox vCP132 expressing the glycoproteins gB, gC and gD of the Kentucky D strain of EHV-1. The vaccine was reconstituted in sterile water (group A) or in a solution of carbomer 4 mg/ml (group B) according to Example 8.

Group C was vaccinated with a commercial inactivated whole EHV vaccine containing, in a dose volume of 1.5 ml, inactivated EHV-1 and EHV-4 valencies and 6 mg of carbomer.

Group D is the control group in which the animals were vaccinated with a recombinant canarypox virus vCP1502 expressing the HA glycoprotein of the Influenza A/equi-1/Prague56 virus (see Example 3) reconstituted in carbomer under the same conditions as for group B.

The vaccines are described in detail in Table 1:

| Groups | Vaccines | Antigens | Diluent/adjuvant | Dose (1 ml) |
|---|---|---|---|---|
| A | vCP132 | EHV-1 | Sterile water | $10^{8.0} TCID_{50}$ |
| B | vCP132 | EHV-1 | Carbopol® 974P | $10^{8.0} TCID_{50}$ |

-continued

| Groups | Vaccines | Antigens | Diluent/ adjuvant | Dose (1 ml) |
|---|---|---|---|---|
| C | Commercial vaccine | EHV-1 EHV-4 | Carbopol ® | $10^{7.3}TCID_{50}$ before inactivation EHV-1 $10^{7.3}TCID_{50}$ before inactivation EHV-4 |
| D | vCP1502 | HA-Prague 56 | Carbopol ® 974P | $10^8TCID_{50}$ |

Each animal received 1 dose of vaccine corresponding to D0 and D35 by deep intramuscular injection into the neck.

On D56, the ponies were challenged by intranasal instillation of $10^5TCID_{50}$ of the Ab4/8 strain of EHV-1.

2. Serological Tests

Neutralization tests SN were carried out according to the technique described in Thompson et al., Equine Vet. J., 8, 58-65, 1976. The EHV-1 virus (RACH) was used as antigen.

The SN titres are expressed as the reciprocal of the serum dilution giving 50% neutralization ($log_{10}$).

3. Virological Monitoring

The expression of the virus was monitored daily over 10 days using nasopharyngeal swabs which were collected in virus transporting medium. The swab extracts were titrated on rabbit kidney cells RK13 in microtitre plates. The titres were calculated using the Karber formula expressed in $log_{10}$ $TCID_{50}$ per 1 ml.

4. Results:

No significant local or systemic reaction was noted following these vaccinations.

The seroneutralization SN antibody mean responses (log 10 of the dilution causing 50% neutralization) are:

| Group | Titre on D.0 | Titre on D.56 (before challenge) |
|---|---|---|
| A | 1.69 ± 0.49 | 1.93 ± 0.15 |
| B | 1.69 ± 0.47 | 2.61 ± 0.42 |
| C | 1.19 ± 0.30 | 2.47 ± 0.32 |
| D | 1.57 ± 0.45 | 1.55 ± 0.37 |

A significant increase in the antibody titre is observed with the vaccine vCP132 in carbomer.

All the 5 control ponies excrete the virus through the nasopharynx. The viral excretion in these nonvaccinated ponies continued for an average of 5 days, with a maximum viral excretion at 4 days post-infection.

All the ponies in groups A, C and D excrete a virus after challenge. By contrast only two ponies out of the 5 ponies in group B vaccinated according to the invention excrete the virus. In addition, the quantity of virus excreted in group B is significantly less than the quantity excreted by the other groups including group C. Likewise, the duration of excretion in the animals in group B is much shorter than in the other groups.

Reference may be made to FIG. 1 and to the area under the curve values given below, which show very clearly the virtual absence of viral excretion in the ponies vaccinated with vCP132 in the presence of carbomer. The result is very significant if it is compared in particular with the commercial vaccine. A significant reduction in viral excretion is observed in the animals in group B compared with the controls, whereas no significant difference is observed between the animals in group C and the controls. This reduction by a remarkable and unexpected level in the excretion of virus is particularly advantageous because of its very favourable indications on the limitation of the transmission of the virus from horse to horse.

Total Virus per Pony (Area under the Curve):

| A: | 17.1 |
|---|---|
| B: | 3.0 |
| C: | 9.7 |
| D: | 16.3 |

Example 10

Vaccination of Horses with the Aid of the Canarypox Vector vCP1533 (see Example 5) Recombinant Expressing the HA Glycoprotein of the Influenza A/equi-2/Newmarket/2/93 Virus in the Presence of Carbomer:

1. Protocol for Immunization and Challenge:

20 ponies (Welsh mountain ponies), 7 to 8 months old having no detectable antibodies against the H3N8 and H7N7 viruses, measured by the SRH (for single radial haemblysis) test were used in this study. The negative status of the animals makes it possible to study, under the best conditions, the efficacy of the various vaccines in terms of humoral response. The ponies were randomly distributed into 4 groups (A to D) of 5 to 6 ponies.

The ponies in group A were vaccinated with the aid of a recombinant canarypox (vCP1533) expressing the HA glycoprotein of the influenza A/equi-2/Newmarket/2/93 virus. This vaccine was reconstituted in a solution containing 4 mg/ml of carbomer, Carbopol® 974P.

Group B was vaccinated with a commercial vaccine containing, in a dose volume of 1.5 ml, a mixture of 3 inactivated strains of influenza, namely Prague/56, Suffolk/89 and Miami/63, tetanus toxoid, as well as carbomer (4 mg) and aluminium hydroxide (2.2 mg) as adjuvants.

Group C was vaccinated with the aid of a vaccine C comprising 2 influenza inactivated valencies, namely Prague/56, Newmarket/2/93 as well as tetanus toxoid in aluminium hydroxide.

Group D was vaccinated with the aid of a recombinant canarypox vector vCP132 seen above and reconstituted with a solution containing 4 mg/ml of carbomer 974P. The latter group served as control for the challenge.

The vaccines are described in detail in Table II:

| Groups | Vaccines | Antigens | Diluent/ adjuvant | Dose (1 ml) |
|---|---|---|---|---|
| A | vCP1533 | HA-Newmarket/2/93 | Carbopol ® 974P | $10^{7.7}TCID_{50}$ |
| B | Commercial vaccine | Prague/56; Suffolk/89 Miami/63; tetanus toxoid | Carbopol ® Al(OH)$_3$ | 15 µg HA of each strain |
| C | Vaccine C | Prague/56; Newmarket/2/93 tetanus toxoid | Al(OH)$_3$ | 15 µg HA of each strain |

-continued

| Groups | Vaccines | Antigens | Diluent/ adjuvant | Dose (1 ml) |
|---|---|---|---|---|
| D | vCP132 | gB, gC, gD-EHV-1 | Carbopol ® 974P | $10^{8.0}$ TCID$_{50}$ |

2 doses of 1 ml of each vaccine were administered to each animal at an interval of 5 weeks by deep intramuscular injection into the neck.

2 weeks after the second vaccination, each pony was infected by exposure to an aerosol obtained from about 20 ml of allantoic fluid for a total of $10^{7.3}$ EID$_{50}$ of influenza A-equi-2-/Sussex/89 virus, using an ULTRA 2000 model spraying device (De Villbiss, Somerset Pa.) as described by Mumford et al, Equine Vet, J., 22: 93-98, 1990.

2. Serological Test:

Samples of whole blood were collected on the following days: 0 (the same day as and before the first vaccination), 7, 14, 35 (the same day as and before the second vaccination), 49 (the same day as and before the challenge), 56 and 63.

The serum was prepared and stored and preserved by freezing at −20° C. until it is used. All the sera were tested for the presence of SRH antibody against Influenza A/equi-1/Prague/56 and Influenza A/equi-2/Newmarket/2/93 as described by Wood et al. (J. Hyg., 90: 371-384, 1983).

The diameters of the haemolysis zones were measured in two directions at right angles using an automated reader. The surface area of the zones was calculated and an increase of 50% was considered as being significant. The titres were expressed in mm$^2$ of haemolysis.

3. Virological Monitoring.

Viral excretion was monitored daily over 10 days by collecting naso pharyngeal swabs in a virus transporting medium. The exudate from each swab was diluted by 10-fold serial dilutions in PBS at pH 7.2 and 0.1 ml of each dilution was inoculated into the allantoic space of 10 day-old embryonated eggs. The viral titre (EID$_{50}$/ml) in the swab extracts was calculated from the haemagglutinating activity in the allantoic fluids collected after incubating the eggs at 34° C. for 72 hours.

4. Results.

No significant local or systemic reaction was observed following the first vaccination with the exception of one horse in group B.

It should be noted that the strains Suffolk and Newmarket are similar (Daly et al., J. Gen. Virol. 1996, 661-671) which makes comparison with the commercial vaccine perfectly valid under the trial conditions.

None of the ponies had a detectable SRH antibody against Influenza A/equi-2/Newmarket/2/93 or Influenza A/equi-1/Prague/56 at the beginning of the study. The serological results 1 week after the first vaccination showed that none of the ponies was previously infected with Influenza (no observable booster effect).

2 weeks after the first vaccination, none of the ponies developed a detectable antibody response against Influenza A/equi-1/Prague/56. In addition, there was no detectable SRH antibody against Influenza A/equi-2/Newmarket/93 in 6 animals out of 6 vaccinated with vaccine C, in 4 animals out of 5 vaccinated with the commercial vaccine B and in the control group D. By contrast, a very high SRH antibody titre was observed in all the 5 ponies vaccinated with canarypox in the presence of the carbomer adjuvant: mean 155.4±32.9.

Table III below presents the results obtained animal per animal as regards the SRH antibody titres.

TABLE III

| | | SRH results (mm$^2$) | | | |
|---|---|---|---|---|---|
| | | PRAGUE | NEWMARKET | | |
| Ponies | Group | (D 0, D 7, D 14) | D 0 | D 7 | D 14 |
| M26 | A | 0 | 0 | 0 | 158.0 |
| M27 | A | 0 | 0 | 0 | 104.2 |
| M28 | A | 0 | 0 | 0 | 160.3 |
| M29 | A | 0 | 0 | 0 | 196.4 |
| M30 | A | 0 | 0 | 0 | 158.0 |
| M31 | B | 0 | 0 | 0 | 0 |
| M32 | B | 0 | 0 | 0 | 0 |
| M33 | B | 0 | 0 | 0 | 0 |
| M34 | B | 0 | 0 | 0 | 0 |
| M35 | B | 0 | 0 | 0 | 81.2 |
| M36 | C | 0 | 0 | 0 | 0 |
| M37 | C | 0 | 0 | 0 | trace |
| M38 | C | 0 | 0 | 0 | 0 |
| M39 | C | 0 | 0 | 0 | 0 |
| M40 | C | 0 | 0 | 0 | trace |
| M41 | C | 0 | 0 | 0 | 0 |
| M42 | D | 0 | 0 | 0 | 0 |
| M43 | D | 0 | 0 | 0 | 0 |
| M44 | D | 0 | 0 | 0 | 0 |
| M45 | D | 0 | 0 | 0 | 0 |
| M46 | D | 0 | 0 | 0 | 0 |

The vaccine according to the invention leads to the appearance of a high antibody titre from 14 days after the first vaccination whereas, overall, for vaccines B and C, the first vaccination does not cause on this date the appearance of antibodies at detectable levels. Such an early production of such a titre is a remarkable and unexpected result which has never been observed before.

Example 11

Vaccination of Horses with the Aid of the Canarypox Vector vCP1502 (see Example 3) Recombinant Expressing the HA Glycoprotein of the Influenza A/equi-1/Prague 56 Virus in the Presence of Carbomer The controls of Example 1, vaccinated with vCP1502, were also monitored from the serological point of view.

Table IV below shows the IHA (inhibition of haemagglutination) titres obtained in the animals immunized with 10$^8$ pfu of vCP1502 with Carbopol® 974P at 0 (1st injection V1) and 35 (2nd injection V2) days.

TABLE IV

| | Anti-H7N7 IHA titres | | | | |
|---|---|---|---|---|---|
| Ponies | Day 0 (V1) | Day 7 | Day 14 | Day 35 (V2) | Day 56 |
| RM16 | 0 | 0 | 128 | 64 | 128 |
| RM17 | 0 | 0 | 32 | 128 | 256 |
| RM18 | 0 | 0 | 16 | 64 | 512 |
| RM19 | 0 | 0 | 32 | 32 | 256 |
| RM20 | 0 | 0 | 128 | 64 | 128 |

As in the preceding example, it is observed that the injection of a canarypox-EIV (expressing the HA gene of the A equi-1/Prague virus) mixed with carbomer allows high specific IHA titres to be obtained from D14 after a vaccination. Remarkably, these high titres are further significantly increased after a booster, reaching a very high mean titre, of a level which has never been observed before for the HA antigen of EIV H7N7 virus on horses which have not undergone promostimulation.

Example 12

Application in Cats

The recombinant virus tested is a recombinant canarypox virus expressing the gB, gC and gD genes of the feline herpesvirus (Feline Herpesvirus=FHV). This recombinant virus is identified vCP243 (see Example 7).

The protocol for vaccination/challenge in the FHV model is the following.

| Group | Number of cats | Vaccine | Diluent/ adjuvant | Dose |
|---|---|---|---|---|
| A | 6 | vCP243 | water | $10^{7.5}$ pfu |
| B | 6 | vCP243 | Carbopol ® 974P | $10^{7.5}$ pfu |
| C | 6 | CORIFELIN ® | — | 1 commercial dose |
| D (controls) | 6 | — | — | — |

The cats are vaccinated on D0 and D28 by the subcutaneous route.

The vaccine CORIFELIN® is a subunit FHV vaccine marketed by Mérial, Lyon, France, comprising at least 200 IDR units of FHV viral fractions, 25 µg of purified feline calicivirus antigen, 0.1 mg of thiomersal and the oily excipient QS 1 ml.

The challenge, is carried out on D49, by the oronasal route for an FHV challenge strain.

The clinical monitoring is carried out for 14 days after challenge, noting the clinical signs (noting of the clinical signs according to the rules of the European Pharmacopoeia).

Protection is assessed after challenge on the following criteria:
  mean clinical scores for each group, compared with each other and with the mean clinical score for the control group
  level of FHV viral excretion after challenge (measurement of the viral load in pharyngeal swabs prepared daily from D0 to D10 after challenge)
  FHV virus neutralizing antibody titres on blood samples collected on D0, D28, D49, D63.

For all these criteria, the mean levels for each group are also compared with each other and with the mean level for the control group.

Example 13

Application in Dogs

The recombinant virus tested is a recombinant canarypox virus expressing the HA and F genes of the Carré's disease virus (Canine Distemper Virus, CDV). This recombinant virus is identified vCP258. (see Example 2).

The protocol for vaccination/challenge in the CDV model is the following.

| Group | Number of dogs | Vaccine | Diluent/ adjuvant | Dose |
|---|---|---|---|---|
| A | 6 | vCP258 | water | $10^{7.0}$ pfu |
| B | 6 | vCP258 | Carbopol ® 974P | $10^{7.0}$ pfu |
| C | 6 | EURICAN ® | — | 1 commercial dose |
| D (controls) | 6 | — | — | — |

The dogs are vaccinated on D0 and D28 by the subcutaneous route.

The vaccine EURICAN® (CHPPI2) is a live vaccine marketed by Mérial, Lyon, France. One commercial dose contains a minimum of $10^4$ pfu of the CDV Onderstepoort vaccinal strain.

The challenge is made on D56 by intracranial administration of a 1/10 dilution of the CDV "Snyder-Hill" challenge strain (batch prepared and provided by USDA). Clinical monitoring is performed for 21 days after challenge, noting the clinical signs (noting of the clinical signs according to the rules of the European Pharmacopoeia).

Protection is assessed after challenge on the following criteria:
  mean clinical scores for each group, compared with each other and with the mean clinical score of the control group
  CDV viraemia level after challenge (measurement of the viral load in the lymphocytes on D56, D61, D63, D66, D70, D77)
  CDV virus neutralizing antibody titres on D0, D14, D28, D42, D56, D63, D77.

For all these criteria, the mean levels for each group are also compared with each other and with the mean level for the control group.

Example 14

Vaccination of Horses with a Single Dose of the Canary Pox Vectors vCP1533 and vCP1529 Recombinants (see Examples 4, 5 and 10) in the Presence of Carbomer:

1. Protocol for Immunization and Challenge:

10 Welsh Mountain ponies, 12 to 15 months-old and seronegative to influenza (no detectable antibodies to either Influenza A/equi-2/Newmarket/2/93 or Influenza A/equi-2/Newmarket/1/93 by SRH test) were randomly divided into two groups of 5 animals each.

Each animal in the test group was vaccinated on day zero with a single 1 ml dose of a vaccine containing 7.48 $\log_{10}$ FAID$_{50}$ (fluorescence assay infectious dose 50 percent) of a recombinant canarypox virus containing and expressing the HA glycoprotein of Influenza A/equi-2/Newmarket/2/93 (VCP1533), 7.53 $\log_{10}$ FAID$_{50}$ of a recombinant canarypox virus containing and expressing the HA glycoprotein of Influenza A/equi-2/Kentucky/94 (VCP1529) and 4 mg of Carbomer 974P per ml. The vCP1529 and vCP1533 recombinants were as described in Examples 4 and 5 herein, respectively. The vaccine was delivered by deep intramuscular injection.

The five animals in the control group remained unvaccinated.

All the ponies are challenged on Day 14 by exposure to an aerosol generated from approximately 20 ml of allantoic fluid containing 6.3 $\log_{10}$ $EID_{50}$ (Egg Infectious dose 50 percent) per ml of influenza A/equi-2/Newmarket/5/03 using a model ULTRA NEB 2000 (DeVillbiss, Somerset, Pa.). Following vaporization, the ponies were held in the challenge box for at least an additional 60 minutes.

2. Serological Test

Samples of whole blood were collected on the following days: 0 (the same day as and before the vaccination), 14 (the same day as and before challenge), 21 and 28.

The serum was prepared and stored at −20° C. until used. All sera samples were tested for the presence of SRH antibody against Influenza A/equi-2/Newmarket/2/93 and Influenza A/equi-2/Newmarket/1/93 as previously described.

The diameters of the haemolysis zones were measured in two directions at right angles using an automated reader. The surface area of the zones was calculated and an increase of 50% or 25 mm² was considered significant. The titres were expressed in mm² of haemolysis.

3. Virological Monitoring

Viral excretion was monitored daily over 10 days by collecting naso swabs in a virus transporting medium as previously described. The exudates from each swab was diluted by 10-fold serial dilutions in PBS at pH 7.2 and 0.1 ml of each dilution was inoculated into the allantoic space of 10 day-old embryonated eggs. The viral titre (EID50/ml) in the swab extracts was calculated from the haemagglutinating activity in the allantoic fluids collected after incubating the eggs at 34° C. for 72 hours.

4. Symptom Monitoring

Each pony was examined each of the 14 days following challenge for the occurrence of symptoms associated with equine: influenza: fever, lethargy, anorexia, coughs and nasal discharge, as well as general condition.

The presence of anorexia was indicated by a score of 1, absence of anorexia received a score of 0.

Dyspnea was indicated as present by a score of 1, or absent by a score of 0.

Nasal discharge was scored on the basis of intensity, extent and type:

| | |
|---|---|
| Intensity: | absent (0);<br>slight discharge when looking into the nose (1);<br>moderate discharge readily observed when looking at the nares (2); copious discharge with large collections of discharge in the nares (3). |
| Extent: | unilateral - U (1);<br>Bilateral - B (2). |
| Type: | serous discharge - SD (1);<br>mucopurulent discharge - MPD (2). |

A daily score was calculated as the average of the scores for intensity, extent and type (I+E+T)/3.

Scores for temperature were based on the designation of a temperature over 38.9° C. as hyperthermia. Accordingly, a temperature of below 38.9° C. received a score of 0, and a temperature equal to or greater than 38.9° C. received a score of 1.

The absence of a cough was given a score of 0. The presence of a slight cough, at a frequency of once in 20 minutes, received a score of 1. The presence of a moderate cough, at a frequency of two or more occurances in 20 minutes, received a score of 2.

The general condition of each animal was also monitored, with a score of 0 for normal, apathy received a score of 1, depressed received a score of 2, and prostrated received a score of 3.

5. Results

The results clearly demonstrated protection against symptoms and viral excretion after a single, 1 ml dose of the vaccine. By day 14, prior to challenge, the animals of the vaccinated group had developed significant antibodies against Influenza A/equi-2/Newmarket/2/93 and Influenza A equi-2/Newmarket/1/93 which continued to rise in the two weeks after challenge. In contrast, at day 21, 7 days after challenge, the control group had significantly lower antibody titres. The antibody titre results are depicted in tables VII and VIII.

TABLE VII

SRH TEST RESULTS (mm2) ANTIGEN: NEWMARKET/2/93

| GROUP | FOAL | Day 0 | Day 14 | Day 21 | Day 28 |
|---|---|---|---|---|---|
| Vaccinated | M048 | 0.0 | 87.9 | 65.3 | 117.6 |
| | M049 | 0.0 | 119.6 | 155.7 | 106 |
| | M050 | 0.0 | 115.6 | 100.4 | 113.6 |
| | M051 | 0.0 | 107.9 | 149 | 162.6 |
| | M052 | 0.0 | 82.8 | 136 | 158 |
| | MEAN | 0.0 | 102.8 | 121.3 | 131.6 |
| | SD | 0.0 | 16.5 | 37.9 | 26.6 |
| Control | M053 | 0.0 | 0.0 | 15.8 | 164.9 |
| | M054 | 0.0 | 0.0 | 38.3 | 181.5 |
| | M055 | 0.0 | 0.0 | 47.0 | 164.9 |
| | M056 | 0.0 | 0.0 | 48.3 | 142.4 |
| | M057 | 0.0 | 0.0 | 33.6 | 151.2 |
| | MEAN | 0.0 | 0.0 | 36.6 | 161.0 |
| | SD | 0.0 | 0.0 | 13.1 | 14.9 |

TABLE VIII

SRH TEST RESULTS (mm2) ANTIGEN: NEWMARKET/1/93

| GROUP | FOAL | Day 0 | Day 14 | Day 21 | Day 28 |
|---|---|---|---|---|---|
| Vaccinated | M048 | 0.0 | 89.6 | 111.7 | 109.8 |
| | M049 | 0.0 | 162.6 | 149 | 186.4 |
| | M050 | 0.0 | 149 | 140.3 | 136 |
| | M051 | 0.0 | 151.2 | 140.3 | 149 |
| | M052 | 0.0 | 111.7 | 171.9 | 162.6 |
| | MEAN | 0.0 | 132.8 | 142.6 | 148.8 |
| | SD | 0.0 | 30.8 | 21.6 | 28.7 |
| Control | M053 | 0.0 | 0.0 | 45.7 | 209.2 |
| | M054 | 0.0 | 0.0 | 76.2 | 164.9 |
| | M055 | 0.0 | 0.0 | 38.3 | 158.0 |
| | M056 | 0.0 | 0.0 | 40.7 | 171.9 |
| | M057 | 0.0 | 0.0 | 102.2 | 160.3 |
| | MEAN | 0.0 | 0.0 | 60.6 | 172.9 |
| | SD | 0.0 | 0.0 | 27.8 | 21.0 |

Furthermore, the total clinical scores for each group demonstrate that the vaccinated animals experienced no hyperthermia, no dyspnea no cough and with 3 out of 5 animals only with slight nasal discharge during one day. In contrast, 4 of the 5 control animals experienced significant nasal discharge, as well as dypsnea, cough and hyperthermia. The total scores for each group are depicted in table IX, and are illustrated in FIG. 4.

TABLE IX

CLINICAL SCORES

| GROUP | Gen. Condition | Anorexia | Nasal discharge | Dypsnea | Cough | Total |
|---|---|---|---|---|---|---|
| Vaccinated | 0 | 0 | 11 | 0 | 0 | 11 |
| Control | 0 | 0 | 72 | 16 | 85 | 173 |

Additionally, no virus excretion was found in the vaccinated animals. In contrast, all control animals showed virus excretion ranging from 0.4 to 2.9 during the eight days after challenge. Table X contains the virus excretion results from the nasal swabs.

TABLE X

VIRUS ISOLATION FROM NASAL SWABS (log10 EID50/ml)

| GROUP | FOAL | Day 15 | Day 16 | Day 17 | Day 18 | Day 19 | Day 20 | Day 21 | Day 22 | Day 23 | Day 24 |
|---|---|---|---|---|---|---|---|---|---|---|---|
| Vaccinated | M048 | 0 | 0 | 0 | 0 | 0 | 0 | 0 | 0 | 0 | 0 |
|  | M049 | 0 | 0 | 0 | 0 | 0 | 0 | 0 | 0 | 0 | 0 |
|  | M050 | 0 | 0 | 0 | 0 | 0 | 0 | 0 | 0 | 0 | 0 |
|  | M051 | 0 | 0 | 0 | 0 | 0 | 0 | 0 | 0 | 0 | 0 |
|  | M052 | 0 | 0 | 0 | 0 | 0 | 0 | 0 | 0 | 0 | 0 |
|  | MEAN | 0.0 | 0.0 | 0.0 | 0.0 | 0.0 | 0.0 | 0.0 | 0.0 | 0.0 | 0.0 |
| Control | M053 | 0 | 2.5 | 2 | 2.5 | 3 | 2.5 | 2.5 | 3.5 | 0 | 0 |
|  | M054 | 0 | 0 | 2.5 | 0 | 2.5 | 1.5 | 2.5 | 0 | 0 | 0 |
|  | M055 | 0 | 3.5 | 3.5 | 2 | 2.5 | 2.5 | 0 | 0 | 0 | 0 |
|  | M056 | 0 | 1.5 | 4 | 3 | 3 | 1.5 | 1.5 | 0 | 0 | 0 |
|  | M057 | 2 | 2 | 2.5 | 2.5 | 3.5 | 3 | 1 | 0 | 0 | 0 |
|  | MEAN | 0.4 | 1.9 | 2.9 | 2.0 | 2.9 | 2.2 | 1.5 | 0.7 | 0.0 | 0.0 |

The invention claimed is:

1. A vaccine composition against influenza virus in an equine host comprising at least one recombinant virus, selected from the group consisting of canarypox virus, fowlpox virus and pigeonpox virus, containing and expressing in the equine host at least one nucleic acid molecule encoding at least one heterologous influenza protein; and, as an adjuvant, a polymer having monomeric units of the formula:

$$\begin{array}{c} R_1 \\ | \\ -C-(CH_2)_x-C-(CH_2)_y- \\ | \\ COOH \end{array} \begin{array}{c} R_2 \\ | \\ COOH \end{array}$$

in which $R_1$ and $R_2$ are identical or different and are H or $CH_3$; x is 0 or 1; y is 1 or 2; and x+y=2, or alternatively, as an adjuvant, a polymer of acrylic or methacrylic acid, wherein a single dose of the composition provides immunity against influenza virus.

2. The vaccine composition of claim 1 wherein the recombinant virus is a recombinant canarypox virus.

3. The vaccine composition of claim 1 wherein the equine influenza protein comprises equine influenza HA protein.

4. The vaccine composition of claim 3 wherein the recombinant virus is a canarypox virus.

5. The vaccine composition of claim 1 which comprises two or three recombinant canarypox viruses, each of which contains a nucleic acid molecule that encodes, and each of which expresses, an influenza HA protein from a different influenza strain.

6. The vaccine composition of claim 1 which comprises a recombinant canarypox virus that contains nucleic acid molecules that encode, and that expresses, two or three different influenza HA proteins, each of which is from a different strain of influenza virus.

7. The vaccine composition of claim 5 or 6, wherein at least one recombinant canarypox virus contains a nucleic acid molecule that encodes and expresses an influenza HA protein from Influenza A/equi-2/Newmarket/2/93.

* * * * *

SEQUENCE LISTING

<160> NUMBER OF SEQ ID NOS: 31

<210> SEQ ID NO 1
<211> LENGTH: 1698
<212> TYPE: DNA
<213> ORGANISM: Equine Influenza Virus, Newmarket 2/93 Strain

<400> SEQUENCE: 1

```
atgaagacaa ccattatttt gatactactg acccattggg tctacagtca aaacccaacc      60
agtggcaaca acacagccac attatgtctg ggacaccatg cagtagcaaa tggaacattg     120
gtaaaaacaa taactgatga ccaaattgag gtgacaaatg ctactgaatt agttcagagc     180
atttcaatag ggaaaatatg caacaactca tatagagttc tagatggaag aaattgcaca     240
ttaatagatg caatgctagg agaccccac tgtgatgtct ttcagtatga gaattgggac     300
ctcttcatag aaagaagcag cgctttcagc aattgctacc catatgacat ccctgactat     360
gcatcgctcc ggtccattgt agcatcctca ggaacattgg aattcacagc agagggattc     420
acatggacag gtgtcactca aaacggaaga agtggagcct gcaaaagggg atcagccgat     480
agtttcttta gccgactgaa ttggctaaca aaatctggaa actcttaccc cacattgaat     540
gtgacaatgc ctaacaataa aaatttcgac aaactataca tctgggggat tcatcacccg     600
agctcaaacc aacagcagac agaattgtac atccaagaat caggacgagt aacagtctca     660
acaaaaagaa gtcaacaaac gataatccct aatatcggat ctagaccatg ggtcagggt     720 caatcaggca ggataagcat atactggacc attgtaaaac ctggagatat cctaatgata     780
aacagtaatg gcaacttagt tgcaccgcgg ggatatttta aattgaaaac agggaaaagc     840
tctgtaatga gatcagatgc acccatagac attgtgtgt ctgaatgtat tacaccaaat     900
ggaagcatcc ccaacgacaa accatttcaa aatgtgaaca agttacata tggaaaatgc     960 cccaagtata tcaggcaaaa cactttaaag ctggccactg ggatgaggaa tgtaccagaa    1020
aagcaaatca gaggaatctt tggagcaata gcgggattca tagaaaacgg ctgggaagga    1080
atggttgatg gtggtatgg attccgatat caaaactcgg aaggaacagg acaagctgca    1140
```

```
gatctaaaga gcactcaagc agccatcgac cagattaatg gaaaattaaa cagagtgatt    1200
gaaaggacca atgagaaatt ccatcaaata gagaaggaat tctcagaagt agaagggaga    1260
atccaggact tggagaagta tgtagaagac accaaaatag acctatggtc ctacaatgca    1320
gaattgctgg tggctctaga aaatcaacat acaattgact taacagatgc agaaatgaat    1380
aaattattcg agaagactag acgccagtta agagaaaacg cggaagacat gggaggtgga    1440
tgtttcaaga tttaccacaa atgtgataat gcatgcattg gatcaataag aaatgggaca    1500
tatgaccatt acatatacag agatgaagca ttaaacaacc gatttcaaat caaaggtgtt    1560
gagttgaaat caggctacaa agattggata ctgtggattt cattcgccat atcatgcttc    1620
ttaatttgcg ttgttctatt gggtctcatt atgtgggctt gccaaaaagg caacatcaga    1680
tgcaacattt gcatttga                                                 1698

<210> SEQ ID NO 2
<211> LENGTH: 2956
<212> TYPE: DNA
<213> ORGANISM: Feline Herpesvirus

<400> SEQUENCE: 2
atgtatggtt actggctgga atgtgttatt tgtacagtca tatgtaatgt accactcaac      60
acgatatatt tatatcgcgg ttgtgtctaa taactgtttt taaataaaga gataagtcga     120
aatcacaggc agtgaaatgc cttaaaaatg ggtctcctgt ctatgttagg aatctcttat     180
tttaagtagt cccgcgagac gatttacatc ccgggatcac caacaatctg cgatgagacg     240
atataggatg ggacgcggaa tctaccttct ctatatctgt ctgttatata catatctcca     300
gtttggtact tcgtcgacaa ccgcggtcag tattgaaaat agtgataata gtactgcgga     360
gatgttatca tctaccagca tgtccgctac caccccgata tcccagccaa catctccatt     420
cactactcca actagaagat ctacaaatat agctacaagt tcgagtacca cccaggcatc     480
ccagccaaca tctacattaa ctactctaac tagaagctcg acaactatag ctacaagtcc     540
gagtaccacc caggcagcca cattcatagg atcatctacc gattccaata ccactttact     600
caaaacaaca aaaaaaccaa agcgtaaaaa gaataagaat aacggggcca gatttaaatt     660
agattgtgga tataagggg ttatctacag accgtatttt agccctcttc agctaaactg     720
tactctaccc acagaacctc atattaccaa ccctattgac ttcgagatct ggtttaaacc     780
acgcaccaga tttgggggatt tcttggggga taaagaagac ttcgtaggga atcatacccg     840
caccagcata ttactattta gcagccgtaa tgggagtgtt aattccatgg atcttgggga     900
cgcgacactc gggatcctac aatctaggat accagattac acattatata atattcccat     960
acaacatacc gaagcgatgt cattgggaat caaatctgtg gaatctgcca cgtccggtgt    1020
ttatacatgg cgggtctatg gtggagatgg actaaataaa acagtgctag acaggtaaa    1080 tgtatctgta gtggcatatc ccccccgag cgtaaatctt acaccacgcg ccagtctatt    1140
taataagacc tttgaggcgg tatgtgcagt ggcgaattac ttcccgcgat ccacgaaact    1200
aacatggtat cttgacggga agccaataga aaggcaatac atttcagata cggcaagtgt    1260
atggatagat ggactcatca ccagaagttc tgtgttggct attccgacaa ctgaaacaga    1320
ttccgagaaa ccagatatac gatgtgattt ggaatggcat gaaagtcctg tgtcctataa    1380
gagattcacg aaaagtgtag ccccggacgt ctattaccca cctactgtgt ctgttacctt    1440
cgctgataca cgggctatat gtgatgttaa atgtgtacca cgggacggga tatccttgat    1500
```

-continued

```
gtggaaaatt ggtaactacc atctaccaaa agcaatgagt gctgatatac tgatcacagg    1560
tccgtgtata gaacgtccag gtttggtcaa cattcagagt atgtgtgata tatcagaaac    1620
ggatggaccc gtgagttata cctgtcagac catcggatac ccaccaattc taccgggatt    1680
ttacgacaca caagtctacg acgcgtcccc tgaaatcgtc agtgaatcaa tgttggttag    1740
tgtcgttgct gtaatactag gagctgttct catcacagtc tttatcttta ttacggcatt    1800
atgtttatat tattctcatc cccggcgatt ataactctta tagttcgtat aaattactta    1860
tcataaccgt gtttcagcgg ttatattttt ataacagtta attgtttact aatagtttac    1920
aaagtccatc gtttataaaa aacaagccca gtggtattat aatcattcgt atggatataa    1980
accgactcca atccgtgatc tttggtaacc cgcgacgtaa ttactctcac acattttaac    2040
tagtctacga tcacccagat ataataaaaa gattcgcgtg gacatgcaag gtatgaggtc    2100
tacgtcacag ccgttggtcg agataccact ggtagatatg gaaccacagc catctataca    2160
ctccaacgag cctaacccac cgaataaaat gttgacgaca gctatttcat cgcgtaggag    2220 tggaatttt ttatttttctc tgggtatgtt tttttcgga gttatcctaa cagctactat    2280
tatagtatgt acattcatat ttacaatacc agtggatatg ctccagatgc cacgctgccc    2340
tgaggaaacg gtgggtatca aaaactgttg tatccgaccg attagacgcc atgttaaatc    2400
acaccaagat ctagttgcca catgtgccga atacatggaa caacccgccg gccgcatctg    2460
ctgttggagc gcttatacca ttattggaca tcttcaatgg agatgggata tctacaaacg    2520
actctcttta cgattgtatt ctctctgatg aaaaaaaatc gtgtaataca tcaatggccg    2580
tatgtcaatc aacatatctt ccaaatcccc taagtgactt tattatgcgc gttaggcaga    2640
tattttctgg aatcctaaat cattaatcca tttactaaat aaataaacaa taccgtttag    2700
gtaattaaac atgattctag tgtttattgt cgtatgtacg ggcgatgggt ggataacaac    2760
tcgacaatga tcaattatat tgattaacct tgtaataaat tcgtcggatt attggatata    2820
tcgagatgat atcacattat tttctaatag cgtgtgtttg aaagtccacc ctactagtgc    2880
catgtgcgcg tttgatcgaa gaggcattta atgttgccag agtttcaatt ccgtatgtat    2940
cgtcgagtaa tctaga                                                    2956

<210> SEQ ID NO 3
<211> LENGTH: 70
<212> TYPE: DNA
<213> ORGANISM: Equine influenza virus

<400> SEQUENCE: 3
cgcggccatc gcgatatccg ttaagtttgt atcgtaatga acactcaaat tctaatatta    60
gccacttcgg                                                           70

<210> SEQ ID NO 4
<211> LENGTH: 36
<212> TYPE: DNA
<213> ORGANISM: Equine influenza virus

<400> SEQUENCE: 4
cgcgcggcgg taccttatat acaaatagtg caccgc                              36

<210> SEQ ID NO 5
<211> LENGTH: 70
<212> TYPE: DNA
<213> ORGANISM: Equine influenza virus

<400> SEQUENCE: 5
```

```
cgcggccatc gcgatatccg ttaagtttgt atcgtaatga agacaaccat tattttgata    60
ctactgaccc                                                            70

<210> SEQ ID NO 6
<211> LENGTH: 42
<212> TYPE: DNA
<213> ORGANISM: Equine influenza virus

<400> SEQUENCE: 6
cgcgcggcgg tacctcaaat gcaaatgttg catctgatgt tg                        42

<210> SEQ ID NO 7
<211> LENGTH: 40
<212> TYPE: DNA
<213> ORGANISM: Equine influenza virus

<400> SEQUENCE: 7
ttgtcgactc aatcatgaag acaaccatta ttttgatact                           40

<210> SEQ ID NO 8
<211> LENGTH: 34
<212> TYPE: DNA
<213> ORGANISM: Equine influenza virus

<400> SEQUENCE: 8
ttggatcctt actcaaatgc aaatgttgca yctg                                 34

<210> SEQ ID NO 9
<211> LENGTH: 74
<212> TYPE: DNA
<213> ORGANISM: Equine influenza virus

<400> SEQUENCE: 9
ctagttcgcg atatccgtta agtttgtatc gtaatgaaga caaccattat tttgatacta    60
ctgacccatt gggt                                                       74

<210> SEQ ID NO 10
<211> LENGTH: 72
<212> TYPE: DNA
<213> ORGANISM: Equine influenza virus

<400> SEQUENCE: 10
agacccaatg ggtcagtagt atcaaaataa tggttgtctt cattacgata caaacttaac    60
ggatatcgcg aa                                                         72

<210> SEQ ID NO 11
<211> LENGTH: 20
<212> TYPE: DNA
<213> ORGANISM: Feline Herpesvirus

<400> SEQUENCE: 11
gattaaacct aaataattgt                                                 20

<210> SEQ ID NO 12
<211> LENGTH: 42
<212> TYPE: DNA
<213> ORGANISM: Feline Herpesvirus

<400> SEQUENCE: 12
tttttctaga ctgcagcccg ggacatcatg cagtggttaa ac                        42
```

```
<210> SEQ ID NO 13
<211> LENGTH: 18
<212> TYPE: DNA
<213> ORGANISM: Feline Herpesvirus

<400> SEQUENCE: 13
gggtttcaga ggcagttc                                                   18

<210> SEQ ID NO 14
<211> LENGTH: 21
<212> TYPE: DNA
<213> ORGANISM: Feline Herpesvirus

<400> SEQUENCE: 14
atgtccactc gtggcgatct t                                               21

<210> SEQ ID NO 15
<211> LENGTH: 42
<212> TYPE: DNA
<213> ORGANISM: Feline Herpesvirus

<400> SEQUENCE: 15
tttttctaga ctgcagcccg ggacatcatg cagtggttaa ac                         42

<210> SEQ ID NO 16
<211> LENGTH: 21
<212> TYPE: DNA
<213> ORGANISM: Feline Herpesvirus

<400> SEQUENCE: 16
gtggacacat atagaaagtc g                                               21

<210> SEQ ID NO 17
<211> LENGTH: 21
<212> TYPE: DNA
<213> ORGANISM: Feline Herpesvirus

<400> SEQUENCE: 17
caccttcagg atctactgtc g                                               21

<210> SEQ ID NO 18
<211> LENGTH: 24
<212> TYPE: DNA
<213> ORGANISM: Feline Herpesvirus

<400> SEQUENCE: 18
acgcatgatg acaagattat tatc                                            24

<210> SEQ ID NO 19
<211> LENGTH: 18
<212> TYPE: DNA
<213> ORGANISM: Feline Herpesvirus

<400> SEQUENCE: 19
ctgtggaatt cgcaatgc                                                   18

<210> SEQ ID NO 20
<211> LENGTH: 48
<212> TYPE: DNA
<213> ORGANISM: Feline Herpesvirus

<400> SEQUENCE: 20
aaaactgcag cccgggaagc ttacaaaaat tagatttgtt tcagtatc                   48
```

<210> SEQ ID NO 21
<211> LENGTH: 36
<212> TYPE: DNA
<213> ORGANISM: Feline Herpesvirus

<400> SEQUENCE: 21
ggtatggcaa atttctttca gggactcggg gatgtg                                36

<210> SEQ ID NO 22
<211> LENGTH: 17
<212> TYPE: DNA
<213> ORGANISM: Feline Herpesvirus

<400> SEQUENCE: 22
tttatattgt aattata                                                    17

<210> SEQ ID NO 23
<211> LENGTH: 17
<212> TYPE: DNA
<213> ORGANISM: Feline Herpesvirus

<400> SEQUENCE: 23
gtaaaacgac ggccagt                                                    17

<210> SEQ ID NO 24
<211> LENGTH: 21
<212> TYPE: DNA
<213> ORGANISM: Feline Herpesvirus

<400> SEQUENCE: 24
atgatgacac gtctacattt t                                               21

<210> SEQ ID NO 25
<211> LENGTH: 21
<212> TYPE: DNA
<213> ORGANISM: Feline Herpesvirus

<400> SEQUENCE: 25
tgttacataa cgtacttcag c                                               21

<210> SEQ ID NO 26
<211> LENGTH: 18
<212> TYPE: DNA
<213> ORGANISM: Feline Herpesvirus

<400> SEQUENCE: 26
gaggattcga aacggtcc                                                   18

<210> SEQ ID NO 27
<211> LENGTH: 53
<212> TYPE: DNA
<213> ORGANISM: Feline Herpesvirus

<400> SEQUENCE: 27
aattttctcg agaagcttgt taacaaaaat cattaaggat ggtagattgc atg            53

<210> SEQ ID NO 28
<211> LENGTH: 55
<212> TYPE: DNA
<213> ORGANISM: Feline Herpesvirus

<400> SEQUENCE: 28

-continued

```
cattatcgcg atatccgtta agtttgtatc gtaatgagac gatataggat gggac        55
```

<210> SEQ ID NO 29
<211> LENGTH: 18
<212> TYPE: DNA
<213> ORGANISM: Feline Herpesvirus

<400> SEQUENCE: 29

```
actattttca atactgac                                                 18
```

<210> SEQ ID NO 30
<211> LENGTH: 18
<212> TYPE: DNA
<213> ORGANISM: Feline Herpesvirus

<400> SEQUENCE: 30

```
aaatgtgtac cacgggac                                                 18
```

<210> SEQ ID NO 31
<211> LENGTH: 54
<212> TYPE: DNA
<213> ORGANISM: Feline Herpesvirus

<400> SEQUENCE: 31

```
aagaagcttc tgcagaattc gttaacaaaa atcattataa tcgccgggga tgag         54
```